(12) United States Patent
Burnett et al.

(10) Patent No.: US 10,143,408 B2
(45) Date of Patent: *Dec. 4, 2018

(54) METHODS AND DEVICES FOR THE DIAGNOSIS AND TREATMENT OF DIABETES

(71) Applicant: TheraNova, LLC, San Francisco, CA (US)

(72) Inventors: Daniel R. Burnett, San Francisco, CA (US); Evan S. Luxon, Omaha, NE (US); Marcie Hamilton, San Francisco, CA (US); Brian M. Neil, San Francisco, CA (US); Brett D. Mensh, San Rafael, CA (US)

(73) Assignee: TheraNova, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/451,155

(22) Filed: Mar. 6, 2017

(65) Prior Publication Data

US 2017/0172469 A1   Jun. 22, 2017

Related U.S. Application Data

(63) Continuation of application No. 14/303,376, filed on Jun. 12, 2014, now Pat. No. 9,603,558, which is a
(Continued)

(51) Int. Cl.
*A61B 5/00* (2006.01)
*A61B 5/145* (2006.01)
(Continued)

(52) U.S. Cl.
CPC ........ *A61B 5/14507* (2013.01); *A61B 5/1459* (2013.01); *A61B 5/1473* (2013.01);
(Continued)

(58) Field of Classification Search
CPC ................................ A61B 5/14532
See application file for complete search history.

(56) References Cited

U.S. PATENT DOCUMENTS

| 4,271,827 A | 6/1981 | Angelchik |
| 4,557,724 A | 12/1985 | Gregonis et al. |

(Continued)

FOREIGN PATENT DOCUMENTS

| WO | WO 1992/013271 | 8/1992 |
| WO | WO 2003/082363 | 10/2003 |

(Continued)

OTHER PUBLICATIONS

Addington et al., Intra-abdominal Pressures during Voluntary and Reflex Cough, BioMed Central, Cough 2008, 4:2, Apr. 30, 2008.
(Continued)

*Primary Examiner* — Christian Jang
(74) *Attorney, Agent, or Firm* — Levine Bagade Han LLP

(57) ABSTRACT

Methods and devices for the diagnosis and treatment of diabetes are disclosed in which an analyte concentration within a peritoneal fluid of a human subject may be determined by implanting an analyte sensor apparatus in the subject where the apparatus may comprise a housing and a flexible sensing catheter which has a lumen with a plurality of apertures and an exterior surface with an analyte sensor affixed thereto. The catheter may comprise a proximal end attached to the housing and the remaining end may be positioned freely within the peritoneal space to contact peritoneal fluid where an analyte concentration in the peritoneal fluid may be sensed. The housing may be anchored at a subcutaneous site proximate the peritoneal space. The sensed analyte concentration may then be transduced into a transmittable electrical signal.

7 Claims, 32 Drawing Sheets

Related U.S. Application Data continuation of application No. PCT/US2012/069262, filed on Dec. 12, 2012, and a continuation-in-part of application No. PCT/US2008/073279, filed on Aug. 15, 2008, and a continuation-in-part of application No. PCT/US2012/028071, filed on Mar. 7, 2012, said application No. PCT/US2012/069262 is a continuation-in-part of application No. 13/306,335, filed on Nov. 29, 2011, now Pat. No. 9,204,828.

(60) Provisional application No. 61/630,504, filed on Dec. 12, 2011, provisional application No. 61/744,030, filed on Sep. 17, 2012, provisional application No. 61/464,619, filed on Mar. 7, 2011, provisional application No. 61/628,534, filed on Nov. 2, 2011, provisional application No. 61/583,258, filed on Jan. 5, 2012.

(51) Int. Cl.
*A61M 5/172* (2006.01)
*A61B 5/1459* (2006.01)
*A61B 5/1473* (2006.01)
*A61B 5/1486* (2006.01)
*A61M 1/28* (2006.01)
*A61M 5/142* (2006.01)
*A61M 5/14* (2006.01)

(52) U.S. Cl.
CPC ...... *A61B 5/14532* (2013.01); *A61B 5/14865* (2013.01); *A61B 5/4839* (2013.01); *A61M 1/28* (2013.01); *A61M 5/14276* (2013.01); *A61M 5/1723* (2013.01); *A61M 2005/1403* (2013.01); *A61M 2005/1726* (2013.01); *A61M 2205/3306* (2013.01)

(56) References Cited

U.S. PATENT DOCUMENTS

| | | |
|---|---|---|
| 4,581,020 A | 4/1986 | Mittleman |
| 4,702,232 A | 10/1987 | Gardner et al. |
| 4,841,956 A | 6/1989 | Gardner et al. |
| 4,861,341 A | 8/1989 | Woodburn |
| 5,100,392 A | 3/1992 | Orth et al. |
| 5,240,675 A | 8/1993 | Wilk et al. |
| 5,260,020 A | 11/1993 | Wilk et al. |
| 5,263,473 A | 11/1993 | McWhorter |
| 5,295,958 A | 3/1994 | Shturman |
| 5,328,465 A | 7/1994 | Kratoska et al. |
| 5,411,552 A | 5/1995 | Andersen et al. |
| 5,514,079 A | 5/1996 | Dillon |
| 5,549,709 A | 8/1996 | Caspers |
| 5,637,088 A | 6/1997 | Wenner et al. |
| 5,725,593 A | 3/1998 | Caracciolo |
| 5,840,081 A | 11/1998 | Andersen et al. |
| 5,865,729 A | 2/1999 | Meehan et al. |
| 5,897,518 A | 4/1999 | Shaw |
| 5,995,860 A | 11/1999 | Sun et al. |
| 6,039,712 A | 3/2000 | Fogarty et al. |
| 6,053,940 A | 4/2000 | Wijay |
| 6,080,163 A | 6/2000 | Hussein et al. |
| 6,122,536 A | 9/2000 | Sun et al. |
| 6,186,614 B1 | 2/2001 | Nagashima |
| 6,206,831 B1 | 3/2001 | Suorsa et al. |
| 6,264,700 B1 | 7/2001 | Kilcoyne et al. |
| 6,287,253 B1 | 9/2001 | Ortega et al. |
| 6,334,873 B1 | 1/2002 | Lane et al. |
| 6,343,225 B1 | 1/2002 | Clark |
| 6,350,281 B1 | 2/2002 | Rhee |
| 6,447,462 B1 | 9/2002 | Wallace et al. |
| 6,551,280 B1 | 4/2003 | Knighton et al. |
| 6,589,194 B1 | 7/2003 | Calderon et al. |
| 6,648,842 B2 | 11/2003 | Horkel |
| 6,702,857 B2 | 3/2004 | Brauker et al. |
| 6,726,726 B2 | 4/2004 | Caspers |
| 6,790,229 B1 | 9/2004 | Berreklouw |
| 6,815,186 B2 | 11/2004 | Clark |
| 6,875,231 B2 | 4/2005 | Anduiza et al. |
| 7,018,336 B2 | 3/2006 | Enegren et al. |
| 7,056,316 B1 | 6/2006 | Burbank et al. |
| 7,175,652 B2 | 2/2007 | Cook et al. |
| 7,228,160 B2 | 6/2007 | Haight et al. |
| 7,247,138 B2 | 7/2007 | Reghabi et al. |
| 7,351,233 B2 | 4/2008 | Parks |
| 7,726,328 B2 | 6/2010 | Christensen et al. |
| 7,727,147 B1 | 6/2010 | Osorio et al. |
| 7,736,309 B2 | 6/2010 | Miller et al. |
| 7,769,420 B2 | 8/2010 | Silver et al. |
| 8,038,666 B2 | 10/2011 | Triplett et al. |
| 8,147,455 B2 | 4/2012 | Butts et al. |
| 8,292,808 B2 | 10/2012 | Miller et al. |
| 9,238,126 B2 | 1/2016 | Gerrans et al. |
| 2002/0049425 A1 | 4/2002 | Mosel et al. |
| 2002/0066458 A1 | 6/2002 | Aliberto et al. |
| 2003/0114835 A1 | 6/2003 | Noda |
| 2003/0187428 A1 | 10/2003 | Lane et al. |
| 2004/0167415 A1 | 8/2004 | Gelfand et al. |
| 2004/0236395 A1 | 11/2004 | Iaizzo et al. |
| 2005/0107855 A1 | 5/2005 | Lennox et al. |
| 2005/0192627 A1 | 9/2005 | Whisenant et al. |
| 2005/0192654 A1 | 9/2005 | Chanduszko et al. |
| 2006/0030843 A1 | 2/2006 | Lane et al. |
| 2006/0116601 A1 | 6/2006 | Glocker |
| 2006/0275907 A1 | 12/2006 | Glocker |
| 2006/0282175 A1 | 12/2006 | Haines et al. |
| 2008/0039820 A1 | 2/2008 | Sommers et al. |
| 2008/0077043 A1 | 3/2008 | Malbrain et al. |
| 2008/0200850 A1 | 8/2008 | Casalino |
| 2008/0300571 A1 | 12/2008 | LePivert |
| 2009/0018424 A1 | 1/2009 | Kamath et al. |
| 2010/0030133 A1 | 2/2010 | Elia et al. |
| 2010/0121220 A1 | 5/2010 | Nishtala |
| 2011/0144423 A1 | 6/2011 | Tong et al. |
| 2011/0196195 A1 | 8/2011 | Raven et al. |
| 2012/0136343 A1 | 5/2012 | Burnett |
| 2013/0079608 A1 | 3/2013 | Miller et al. |
| 2014/0378791 A1 | 12/2014 | Dehennis et al. |
| 2015/0157248 A1 | 6/2015 | Brauker et al. |

FOREIGN PATENT DOCUMENTS

| | | |
|---|---|---|
| WO | WO 2007/018963 | 2/2007 |
| WO | WO 2008/097609 | 8/2008 |
| WO | WO 2008/103625 | 8/2008 |
| WO | WO 2009/023818 | 2/2009 |
| WO | WO 2009/055435 | 4/2009 |
| WO | WO 2010/141503 | 12/2010 |
| WO | WO 2012/122267 | 9/2012 |
| WO | WO 2013/106155 | 7/2013 |

OTHER PUBLICATIONS

Travers, JP et al., "Assessment of a New One-Layer Adhesive Bandaging Method in Maintaining Prolonged Limb Compression and Effects on Venous Ulcer Healing," *Phlebology*, 7:59-63, 1992.

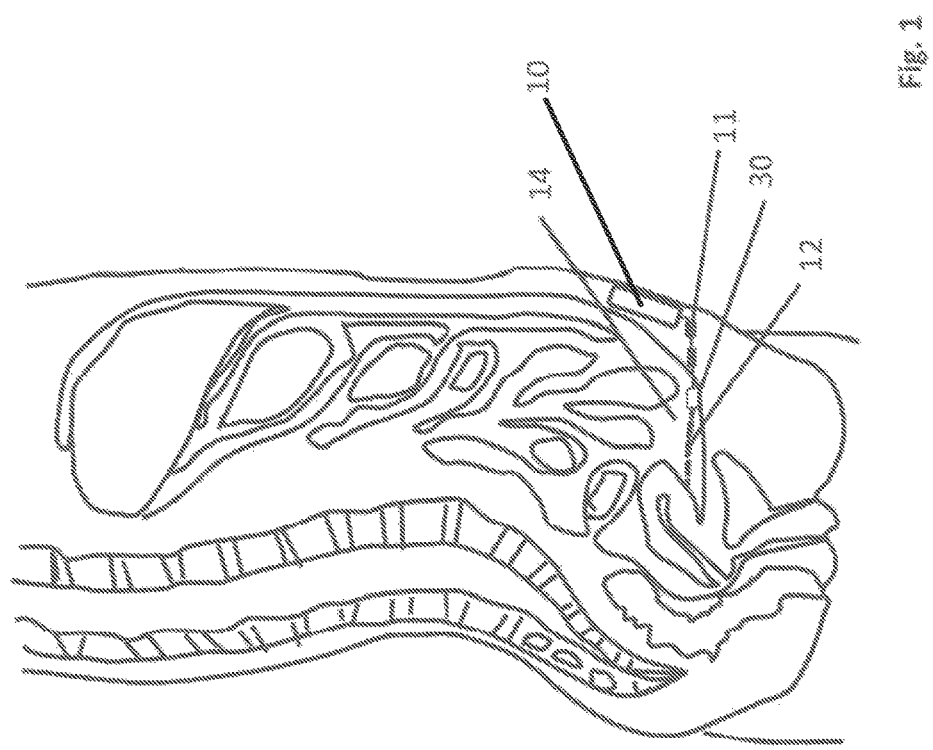

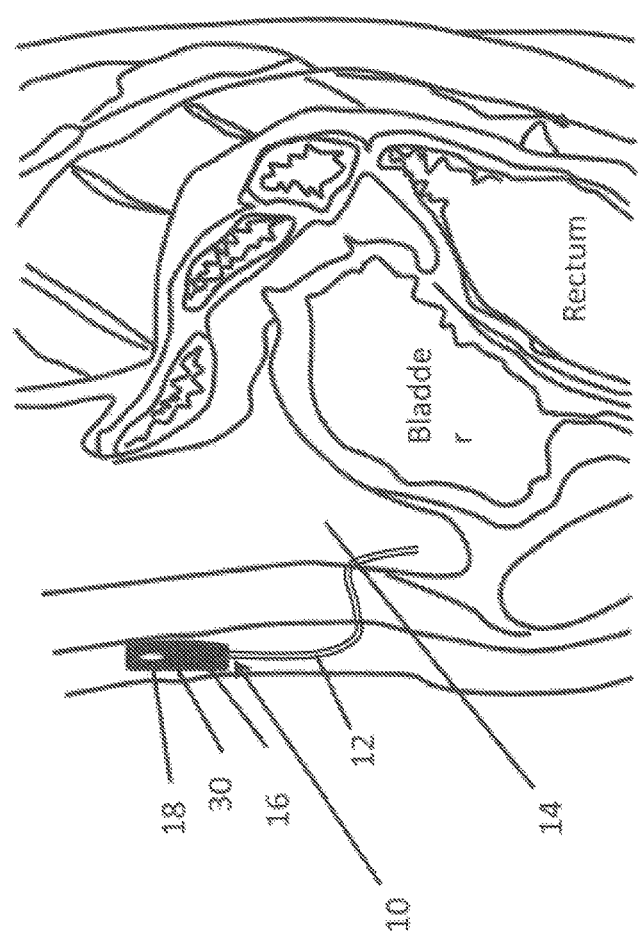

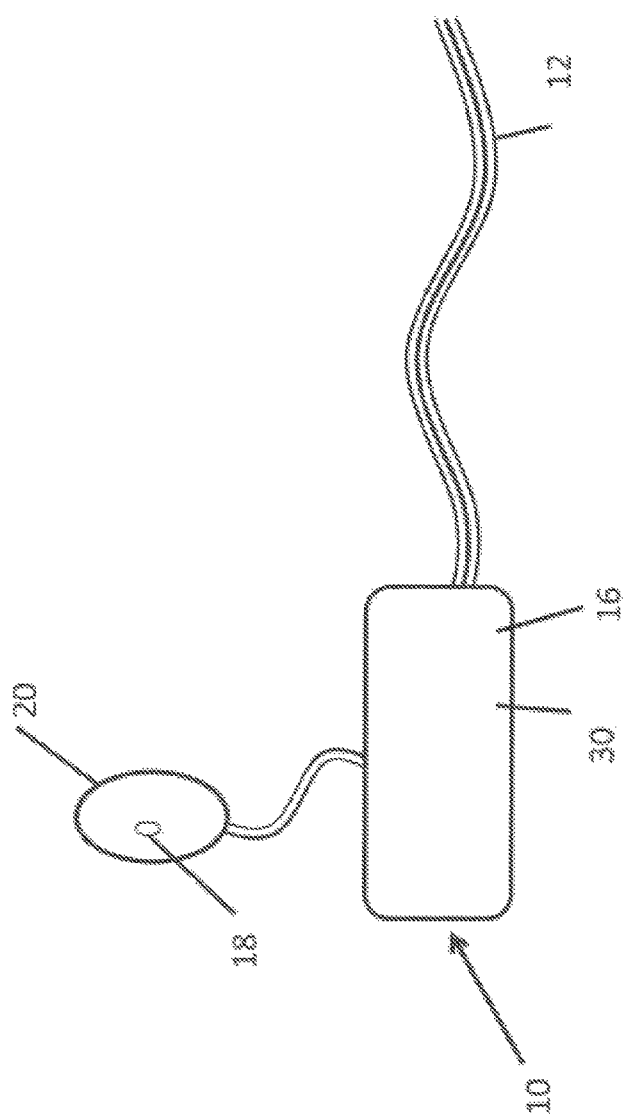

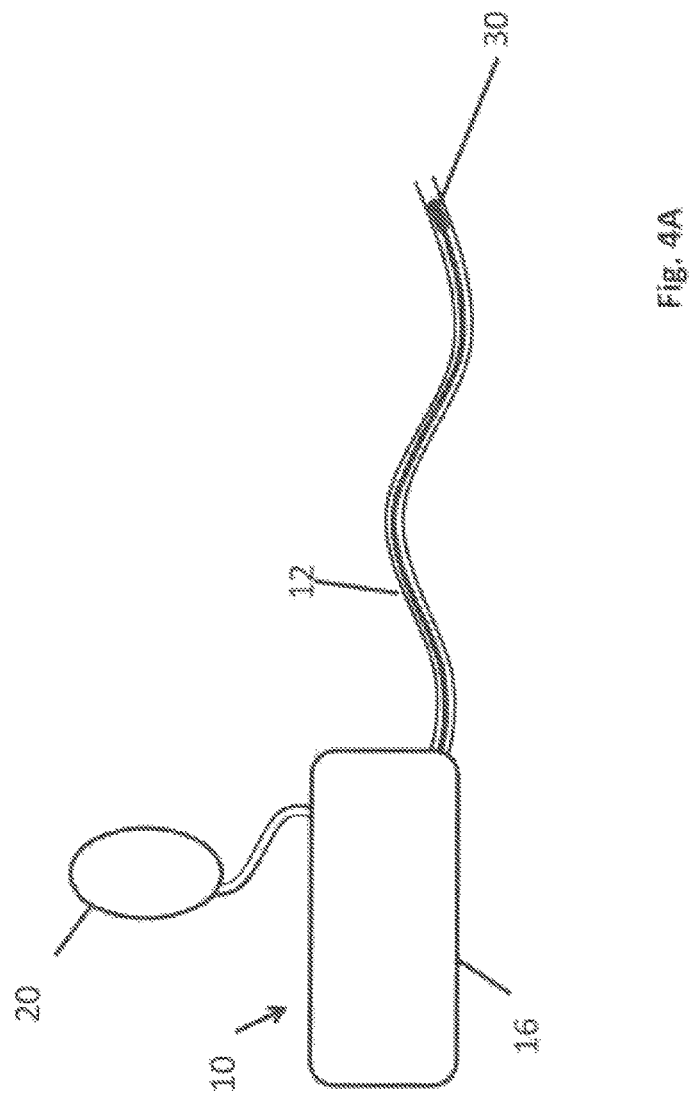

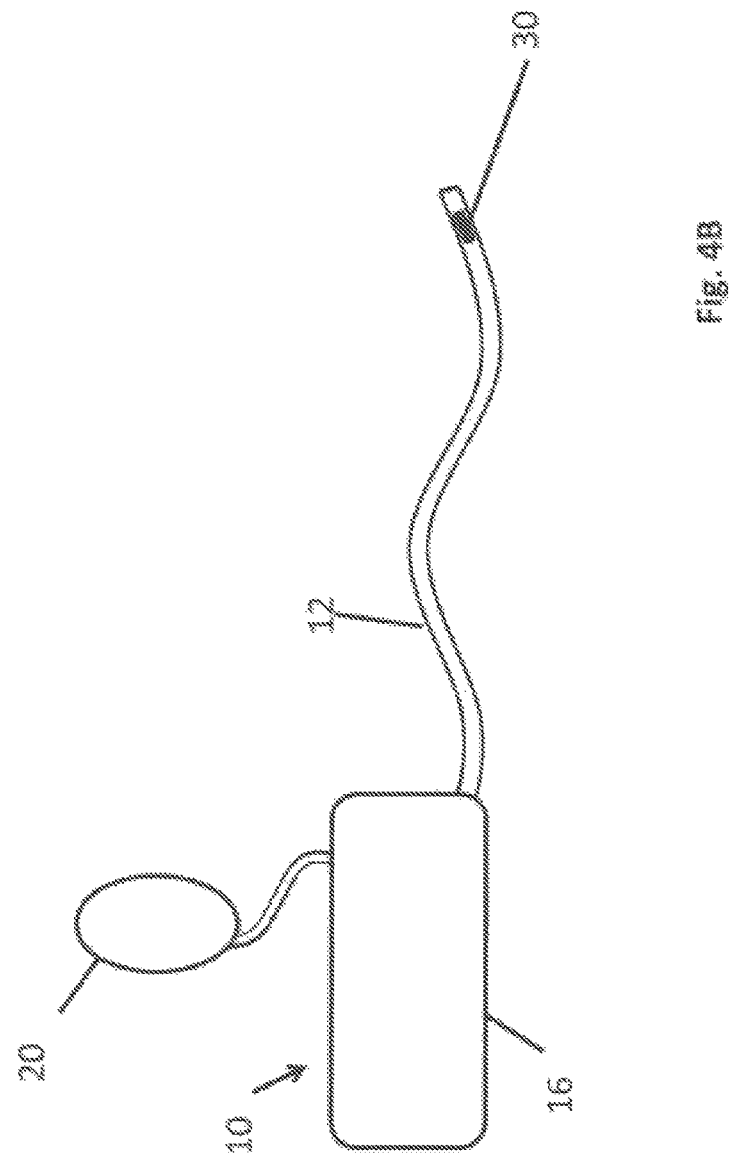

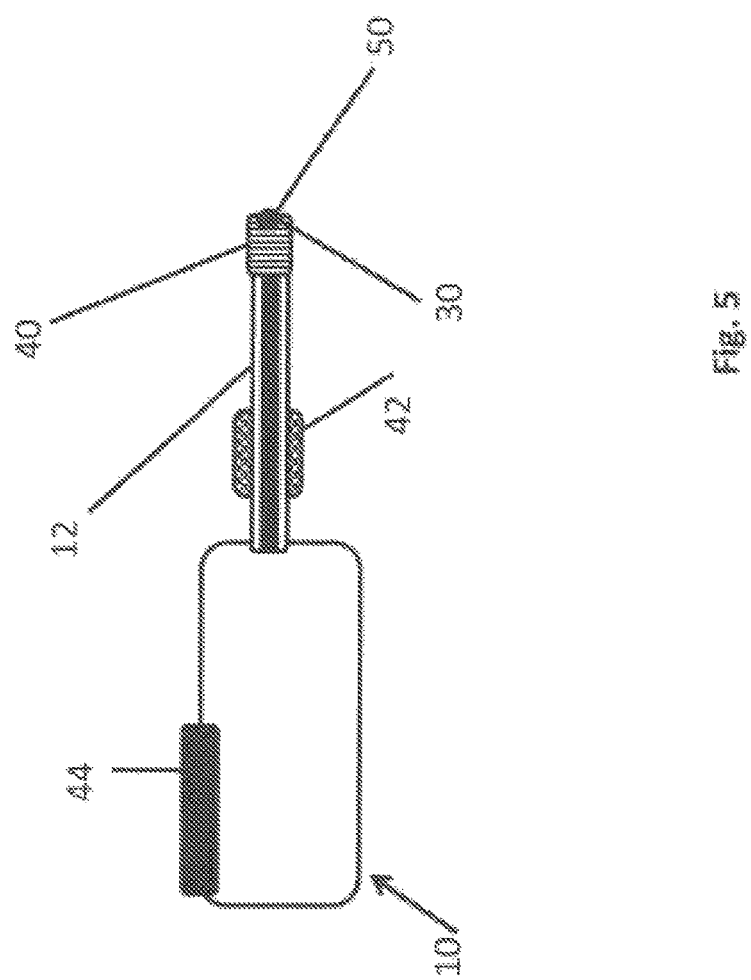

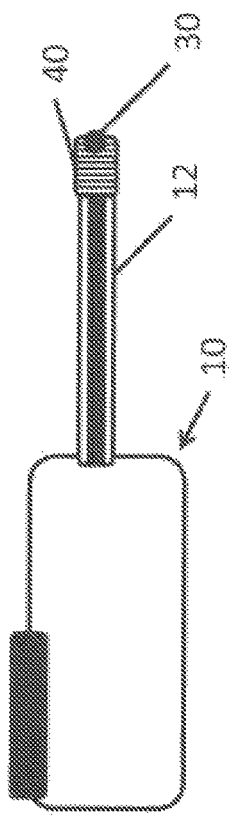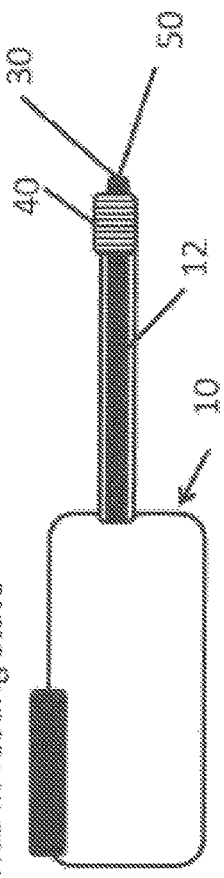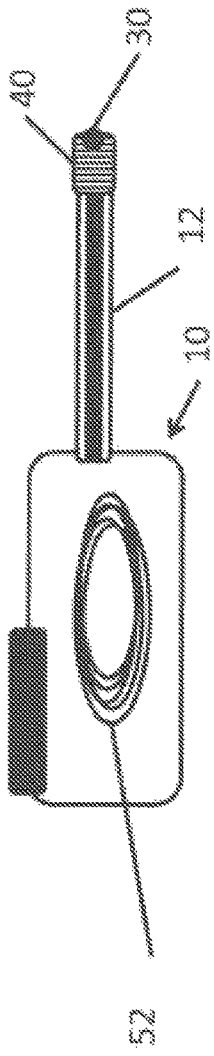
Fig. 6A Device in resting state
Fig 6B Blunt tip of sensor is forced through valve, cleaning the surface of the sensor and reading is taken. If valve or catheter are occluded, flushing port may be used.
Fig 6C Sensor retracts into catheter, again cleaning the sensor

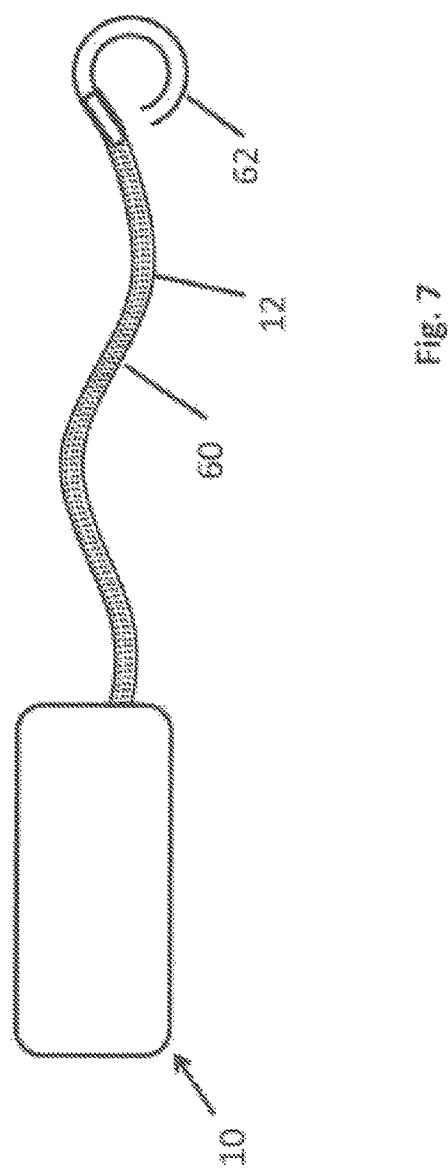

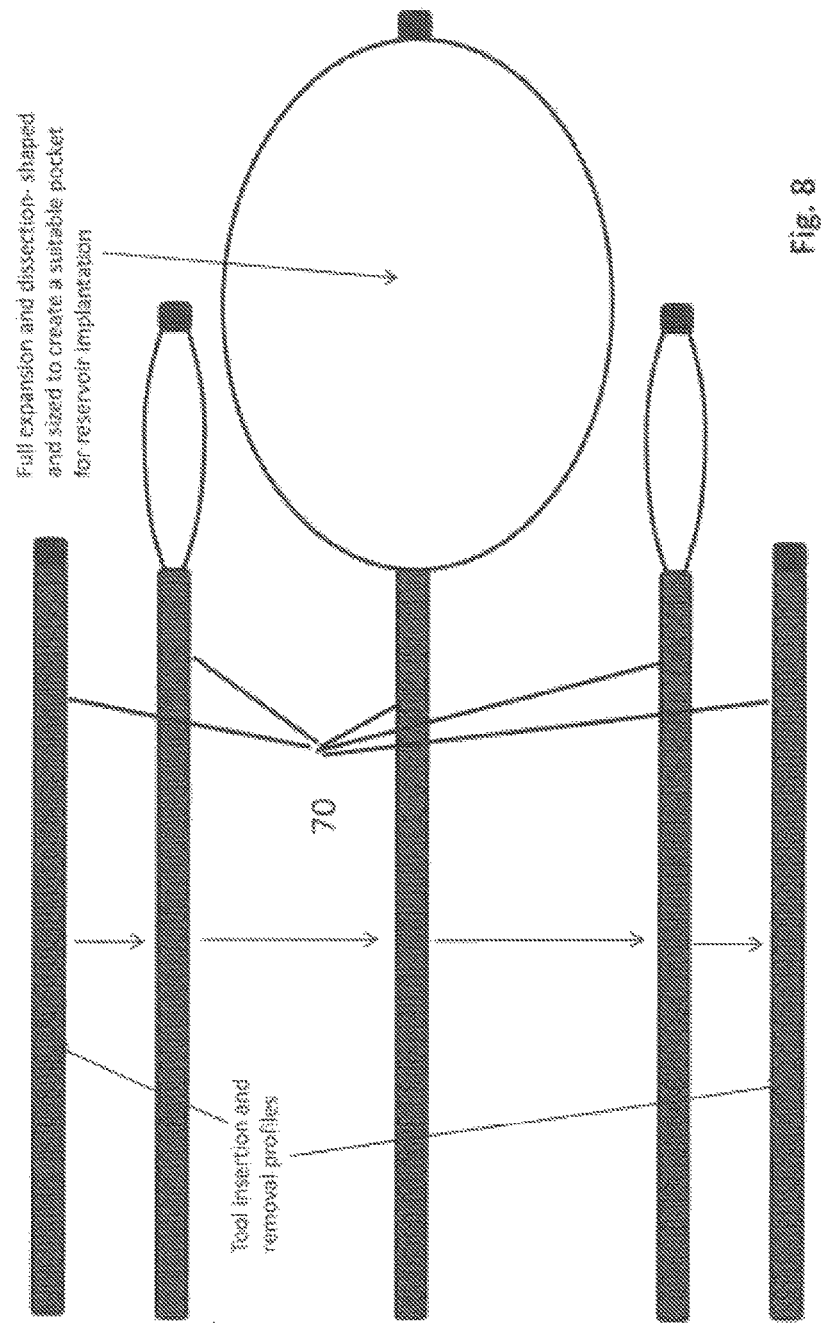

METHODS AND DEVICES FOR THE DIAGNOSIS AND TREATMENT OF DIABETES

CROSS-REFERENCE TO RELATED APPLICATIONS

This application is a continuation of U.S. Ser. No. 14/303,376 filed Jun. 12, 2014, which is a continuation of International Application No. PCT/US2012/069262 filed Dec. 12, 2012, which claims the benefit of priority to U.S. Provisional Application No. 61/360,504 filed Dec. 12, 2011 and U.S. Provisional Application No. 61/744,030 filed Sep. 17, 2012 each of which is incorporated herein by reference in its entirety. International Application No. PCT/US2012/069262 is a continuation-in-part of PCT/US2008/73279 entitled "METHOD AND APPARATUS FOR AUTOMATED ACTIVE STERILIZATION OF FULLY IMPLANTED DEVICES" filed on Aug. 15, 2008, and a continuation-in-part of PCT/US2012/028071 entitled "SENSING FOLEY CATHETER" filed on Mar. 7, 2012, which claims the benefit of U.S. Provisional Application No. 61/464,619 filed Mar. 3, 2011, U.S. Provisional Application No. 61/628,534, filed Nov. 2, 2011, and U.S. Provisional Application No. 61/583,258, filed Jan. 5, 2012. International. Application No. PCT/US2012/069262 is also a continuation-in-part of U.S. Ser. No. 13/306,335 filed Nov. 29, 2011 entitled "CONTINUOUS BLOOD GLUCOSE MONITOR" the full disclosures of each of which are incorporated herein by reference in their entireties.

INCORPORATION BY REFERENCE

All publications and patent applications mentioned in this specification are herein incorporated by reference to the same extent as if each such individual publication or patent application were specifically and individually indicated to be so incorporated by reference.

FIELD OF THE TECHNOLOGY

The disclosed technology relates to continuous analyte monitoring system and implantable drug delivery systems. More particularly, the presently disclosed technology relates to continuous glucose measuring devices that may be implanted in a human subject and which can monitor the glucose concentration in peritoneal fluid, and an implantable insulin reservoir whose operation may be coupled to the implantable continuous glucose monitoring system.

BACKGROUND

Diabetes is a group of diseases characterized by high levels of blood glucose resulting from defects in insulin production, insulin action, or both. Diabetes is the leading cause of blindness in people ages 20 to 70 and is sixth leading cause of death in the United States. Overall, the risk for death among people with diabetes is about 2 times that of people without diabetes. The disease often leads to other complications such as kidney, nerve and heart disease and strokes. It is the leading cause for non-traumatic amputations and kidney failure.

Diabetes is reaching epidemic proportions in the United States. There are approximately 18.2 million people in the United States, or 6.3% of the population, who have diabetes. While an estimated 13 million have been diagnosed with diabetes, 5.2 million people (or nearly one-third) are unaware that they have the disease. Furthermore, diabetes is one of the most common chronic diseases in children and adolescents; about 151,000 people below the age of 20 years have diabetes.

Diabetics must diligently monitor the glucose level in their blood. Blood glucose levels should be maintained between 80 to 120 mg/dl before meals and between 100-140 mg/dl at bedtime. Self-monitoring of blood glucose (SMBG) permits diabetics to know what their blood sugar level is so they can adjust their food, insulin, or activity level accordingly. Improved glucose control can forestall, reduce, or even reverse some of the long-term complications of diabetes.

The gold standard for testing blood glucose is the measurement of glucose in a plasma sample obtained from a vein. A drop of blood is placed on a small window in a test strip. Blood glucose acts as a reagent in a chemical reaction that produces a color change or generates electrons. The color change is detected by a reflectance-meter and reported as a glucose value. Alternatively, the electrons generated in the reaction are detected as an electrical current and reported as a glucose value.

Problems with existing SMBG devices include the requirement of a drop of blood for each test (normally acquired through a prick of the finger). The blood sampling can be painful and cause calluses to form. It also increases the risk for warts and infections. The acute discomfort associated with this presents the largest barrier to life-saving blood glucose control.

Minimally invasive technologies currently on the market in the United States include the GlucoWatch® Biographer (Cygnus Therapeutic Systems Corporation, Redwood City, Calif.) and the Guardian® Continuous Glucose Monitoring System (Medtronic MiniMed, Inc., Northridge, Calif.). The GlucoWatch® Biographer uses reverse iontophoresis, which involves applying an electrical microcurrent to the skin. The current pulls sodium through the intact skin, water follows sodium and water pulls glucose with it. The glucose concentration in this fluid is proportionate to the concentration in blood.

However, there are several problems with this technology. There is a lag time of 20 minutes before a blood glucose value can be reported. The concentration of glucose in the fluid is only 1/1,000 of glucose in the blood. A mild skin discomfort last for a few minutes when the device is first applied to the skin. The device is intended for use only by adults (age 18 and older) with diabetes. It is intended to supplement, not replace, standard home blood glucose monitoring devices. The user also has to calibrate the GlucoWatch® Biographer with a blood glucose value measured on a traditional, i.e. "fingerstick," monitor. Thus a standard (invasive) blood glucose monitor is still required.

The Guardian® Continuous Glucose Monitoring System is designed to automatically and frequently monitor glucose values in subcutaneous interstitial fluid (ISF). It measures ISF glucose every five minutes and it has a hypoglycemia alert. Once inserted, the sensor is virtually painless, but it requires entry of glucose readings from a standard monitor at least twice a day in order to calibrate the sensor. Furthermore, the readings from this monitor lag the actual blood glucose values by 15-20 minutes potentially resulting in over or under dosing of insulin.

Dexcom and Medtronic, among others, market a subcutaneously inserted continuous glucose monitor (CGM), which functions for several clays before requiring replacement. These devices, though, measure interstitial blood glucose, which frequently lags blood glucose by 15 minutes or more. This lag alone is suboptimal (more manageable lag times are in the 5-10 minute range) and lag times may tend to be inconsistent. This means that there is no one control algorithm that can be used to create a closed-loop system since the inter- and intra-sensor variability in lag is too great (5-30 minutes according to recent reports) and doesn't apply to each sensor the same way or even apply to the same sensor during certain physiological situations. For the inter-sensor variability, a sensor is placed at least weekly in the subcutaneous space. During this weekly placement, one sensor may be tightly nestled in a capillary bed (lag time 5-10 min) while the sensor implanted a week later may instead be up against a muscle fiber or a region of fat (30 minute or greater tag time). Therefore a consistent control algorithm for both sensor placements without very poor control is difficult to use.

With respect to intra-sensor variability, there are many conditions that affect blood flow to the submucosa of the skin. Cold temperature, for example, will drastically impact blood flow to the skin. Another potential impact on blood flow is sleeping. There may be significant intra-sensor variability between sleeping and waking lag periods that may have resulted in the episodes of severe nocturnal hypoglycemia with closed loop control noted in the literature.

For the foregoing reasons, there is a need for continuous analyte monitoring systems and implantable drug delivery systems that allow continuous monitoring of glucose levels accurately, for extended periods of time, and with significantly reduced lag times.

SUMMARY OF THE DISCLOSURE

Embodiments of the disclosed technology relate to a device that may be implanted subcutaneously with an attached sampling catheter inserted within the peritoneal cavity of a subject. Generally, one method for determining an analyte concentration within a peritoneal fluid of a human subject may generally comprise implanting an analyte sensor apparatus in the subject, the apparatus comprising a flexible sensing catheter and a housing, the catheter comprising a lumen with a plurality of apertures and an exterior surface with an analyte sensor affixed thereto, the catheter comprising a proximal end attached to the housing, wherein the implanting step comprises positioning the sensing catheter freely within the peritoneal space and anchoring the housing at a subcutaneous site proximate the peritoneal space, contacting the analyte sensor with a peritoneal fluid sample outside the sensing catheter, sensing an analyte concentration in peritoneal fluid sample, and transducing the sensed analyte concentration into a transmittable electrical signal.

Alternatively, the catheter and/or device may be inserted into another space, for example, into a subcutaneous site, or into vascular, peritoneal, cerebrospinal, or pleural spaces. The subcutaneous implant may also be placed in another cavity in order to simplify sensing. The peritoneal fluid that normally collects and/or flows through the peritoneal cavity may be detected by the sampling catheter and analyzed via the device to detect the concentration of glucose within the fluid. The sensor, in one example, may comprise a lens and an emitter that sends out a signal at a predetermined frequency and wavelength as well as a detector that may receive the reflected wavelengths to determine the physiologic characteristics of the peritoneal fluid in proximity or in direct contact with the sensor.

In some embodiments of the technology, a sensor or lens may be cleaned by the intermittent release of a flow of fluid across the sensor/lens using, for example a mechanical pump or an osmotic pump. This fluid can be dedicated for this purpose and stored within the device (or an attached reservoir) or may serve another purpose (e.g., a peritoneal insulin delivery fluid). This fluid may be pumped from its location within the device or associated reservoir and may not require any active powering. A salt or other compound with osmotic activity and limited solubility in water may be stored in concentrated form or solid form in a chamber within the device or associated reservoir. This reservoir may have an externally facing semi-permeable membrane that allows water to flow into the reservoir based on the osmotic gradient established by the dissolving or solubilizing compound. Once the chamber fills to sufficient pressure, a controlled valve, cheek-valve, or other gate may open and allow for the pressurized fluid to course out of the chamber and activate the washing of the sensor or create mechanical action that may power the cleaning action of the sensor.

Active pump, mechanical, insulin delivery, and self-cleaning embodiments are also provided that may be battery powered or inductively powered and/or recharged in order to provide the glucose sensing, insulin delivery and/or cleaning actions. In addition, although the medical field has been slow to exploit the peritoneal space for diagnostic and therapeutic purposes, the peritoneal space is a relatively safe or privileged space for implanted devices with regard the problematic occurrence of fibrosis and tissue reaction sequellae. Further, the concentration of analytes within the plasma are reflected to a lesser or greater degree (depending on molecular size) in the peritoneal fluid. The use of a peritoneal implant to allow for the chronic long-term monitoring of any analyte within the peritoneal fluid may accordingly be advantageous.

Information recorded by the implanted sensor and/or insulin pump may be transmitted wirelessly to an external unit capable of displaying this information. This information may also provide an indication that an intervention may be required. For example, a pressure sensor in line with the flush line may record the pressure and report that an increased pressure is required for the flush. This may trigger either more aggressive automatic flushing/cleaning or may result in the use of an external flush with or without active anti-clogging or anti-clotting agents such as, by way of example heparin or tissue plasminogen activator (TPA).

BRIEF DESCRIPTION OF THE DRAWINGS

FIG. 1 shows an embodiment of the sensing apparatus implanted in a human subject.

FIG. 2 shows an embodiment of the apparatus as it may be implanted in the body.

FIG. 3 shows an embodiment of a sensing apparatus for measuring an analyte in peritoneal fluid.

FIG. 4A shows an embodiment of a sensing apparatus for measuring an analyte peritoneal fluid haying a multi-lumen sampling catheter and an analyte sensor disposed in the distal portion of the catheter.

FIG. 4B shows an embodiment of a sensing apparatus for measuring an analyte in peritoneal fluid having a multi-lumen sampling catheter and an analyte sensor disposed on the exterior surface of the distal portion of the catheter.

FIG. 5 shows an embodiment of a sensing apparatus for measuring an analyte in peritoneal fluid having a valve-tipped catheter with sensor movement past this cleaning valve for taking measurements.

FIGS. 6A-6C show the embodiment of FIG. 5 utilizing the valve tipped catheter.

FIG. 7 shows an embodiment of the sensing apparatus having a semi-permeable membrane embodiment with a curled tip catheter.

FIG. 8 provides a schematic view of an implantation site pocket formation tool at various stages of deployment.

DETAILED DESCRIPTION OF THE INVENTION

Figure 9:
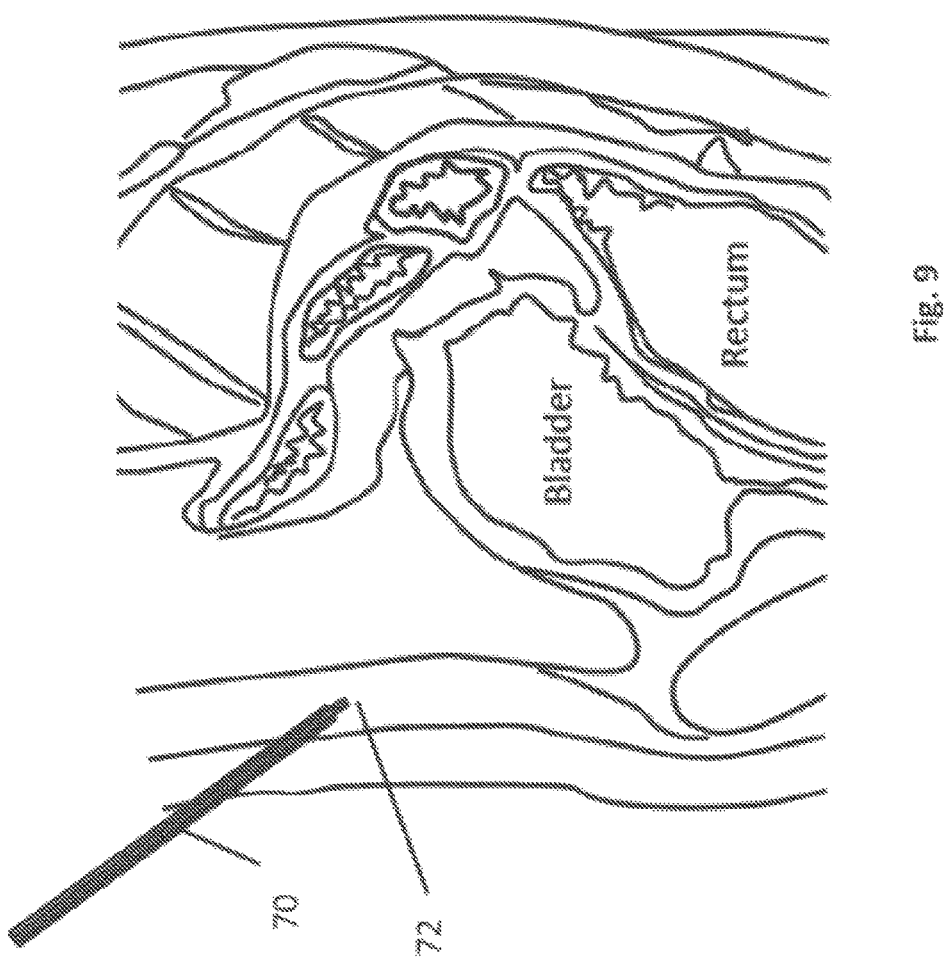
FIG. 9 shows an embodiment of the pocket formation tool entering into preperitoneal implantation site, the tool disposed in a compressed state within a tool insertion catheter.

A device may be implanted subcutaneously with an attached protective or sampling catheter inserted within, e.g., the peritoneal cavity of a subject. Alternatively, the protective or sampling catheter and/or device may be inserted into another space, e.g., subcutaneous, vascular, pre-peritoneal, cerebrospinal, or pleural space. A subcutaneously implanted device may also be placed in another cavity in order to simplify sensing. The peritoneal fluid that normally collects and/or flows through the peritoneal cavity may be detected by the sampling catheter and analyzed via the device to detect the concentration of glucose within the fluid.

A glucose sensor, per embodiments of the disclosed technology, may utilize any one of a variety of modalities including, by way of example, enzymatic sensors, photometric sensors, mid-infrared and near-infrared wavelength sensors, or phosphorescent sensors. More than one modality may be employed, as well, to ensure that results are accurate. A protective sampling catheter and/or the sensor may also be replaced as needed or on a schedule. A subcutaneously implanted device may also be replaced, for example, if its battery requires renewal. These procedures may be conducted in a minimally invasive manner.

Embodiments of the device may also incorporate a sterilizing and/or cleaning mechanism as described in patent application PCT/US2008/73279, entitled "Method and apparatus for automated active sterilization of fully implanted devices", which is herein incorporated by reference in its entirety.

FIG. 1 illustrates one example for placement of the glucose sensing system within the peritoneal cavity 14 of a subject. A glucose sensor assembly 10 may be implanted subcutaneously in proximity to the peritoneal cavity 14 with a sampling catheter 12 attached to the assembly 10 and inserted directly into the peritoneal cavity 14, desirably in the lower half of the peritoneal cavity, i.e. the true pelvis, and/or inserted into a different space such as, by way of example, subcutaneous, vascular, pre-peritoneal, cerebrospinal, pleural spaces, or other anatomical cavities in order to simplify sensing. Ingrowth cuffs 11 allow tissue ingrowth and prevent tracking of infection between cavities.

FIG. 2 shows an embodiment of the apparatus as it may be implanted in the body. The assembly 10 may house a glucose sensor 30 as well as the sensor/measurement electronics and an optional pump 16 or actuator for pumping a therapeutic fluid such as an insulin formulation, as described in further detail below. Optionally, the assembly 10 may also comprise an agitating mechanism and/or sensor clearing/cleaning mechanism (not shown). The sampling catheter 12 may house the glucose sensor 30, desirably affixed to its exterior surface, and may alternatively be positioned at other sites, such the lower half of the pelvis. The apparatus may include art infusion port 18 for intermittent insulin or fluid infusion into pump 16 or peritoneal catheter 12. In a preferred embodiment the peritoneal portion of the catheter 12 ideally will be able to be maintained in the peritoneal cavity 14 during sensor and/or device replacement due to the peritoneal cavity's habituation to the catheter surface.

FIG. 3 illustrates an embodiment of the apparatus having the implantable assembly 10 with sampling catheter 12 attached and extending therefrom. As the catheter 12 resides within the peritoneal cavity 14, the peritoneal fluid may be drawn into the catheter 12 through one or more openings at the tip or along the length of the sampling catheter 12 for measurement by a sensor 30 disposed within the system. Additionally, a fluid reservoir 20 may also be incorporated into the system for providing a fluid for back flushing the sampling catheter 12 intermittently to maintain a clear flow channel.

Sampling catheter 12 may protect the sensor residing within by filtration of fluid drawn into the sampling catheter, thereby providing a substantially debris-free ambient fluid. For this reason, a fluid reservoir 20 (which may also be implanted within the subject) may be optionally attached in fluid communication with assembly 10 or integrated directly with assembly 10 for providing a circulating fluid for intermittently flushing the sensor as well as to clear the sampling catheter line and/or to also ensure adequate exposure of fluid to the peritoneum. Additionally, fluid reservoir 20 may also provide for replenishment of an equilibration fluid that may be infused, allowed to equilibrate, measured for glucose content, and then left in the lumen of the catheter or withdrawn back into the reservoir. In an alternative embodiment the fluid reservoir 20 may also be incorporated into the system for providing insulin into pump 16. In some embodiments, one or more drugs or other active agents may be incorporated into fluid reservoir 20, whose action is directed toward preventing or resolving dogging and/or infection.

FIG. 4A illustrates an embodiment in which a glucose sensor 30 (e.g., an optical sensor) is disposed within the protective or sampling catheter 12. FIG. 4B shows an embodiment in which a glucose sensor 30 (e.g., an optical sensor) is disposed on the exterior surface of the protective or sampling catheter 12. While the sensor 30 is in electrical or wireless communication with the assembly 10 through the sampling catheter 12, sensor 30 may be positioned near or at a distal opening of the sampling catheter 12. Thus, fluid may be circulated through the sampling catheter 12 that may comprise a multi-lumen or single lumen sampling, catheter that allows for intermittent and bidirectional flow of fluid drawn in over the sensor 30 and within an optional pump within assembly 10. Such a pump may urge fluid through the sampling catheter 12 to clean the sensor 30 or sampling catheter 12 via direct mechanical removal of any film or by way of ultrasound or agitation, for example. The pump may be configured to intermittently reverse direction to ensure lumen patency. The sensor 30, in one example, may comprise a lens and an emitter that sends out a signal at a predetermined frequency and wavelength as well as a detector that may receive the reflected wavelengths to determine the physiologic characteristics of the peritoneal fluid in proximity or in direct contact with the sensor 30.

Additionally and/or alternatively in some embodiments, sensor 30 may be moved relative to the assembly 10 and/or sampling catheter 12 (e.g., slide out of the assembly 10 and/or sampling catheter 12 or rotate within the assembly 10 or sampling catheter 12). The sampling catheter 12 may alternatively remain stationary its position and instead be cleaned using, for example, ultrasound or fluid agitation or lavage. In this and other embodiments, one or more flushing ports or reservoirs may be incorporated to provide for cleaning of the system in the event that the system is not in direct contact with the fluid it needs to take its readings.

Reservoir 20 may be intermittently pumped (per a schedule or on demand) by assembly 10 to clear sampling catheter 12 lumen, for example, by flushing or back-flushing the fluid through the sampling catheter 12. Moreover, each of the variations described herein may be optionally inductively recharged and/or refilled with back-flush fluid (or insulin if full artificial pancreas). Furthermore, assembly 10 may also integrate wireless capabilities for providing external communication to transmit data from the glucose sensor 30 to, e.g., an external reader, an insulin pump, etc.

FIG. 5 illustrates an embodiment of a protective sampling catheter 12 that includes a cleaning tip 40 (shown here as a silicone tip) that may function as a valve or window that cleans the sensor 30 in vivo within sampling catheter 12 as it slides or moves past the tip 40. Accordingly, the sensor may be urged to shift or move via an active mechanism housed within assembly 10. The sensor 30 may then return to its resting position between readings where it is protected by the sampling catheter 12 housing. Alternatively, the sensor 30 may be exposed by default and drawn into the sampling catheter 12 only intermittently on a programmed basis or when it senses interference by debris, etc. In the event that the sensor 30 protrudes from the sampling catheter 12, the tip of the sensor 30 may be blunt and atraumatic so as to prevent damage to surrounding tissue. If placed in the peritoneal cavity 14, the device may be positioned such that the end of the sampling catheter 12 and the sensor 30 is in the pelvis and away from the omentum and/or mesentery. If omentum is seen during or prior to placement of a peritoneal sensor, an omentectomy may be performed to improve device reliability.

Additionally, one or more in-growth prevention cuffs 42 may be disposed on the exterior surface of the catheter 12, as shown, to prevent tracking of any infection or fluid between the sensing catheter 12 (which may be in the subcutaneous, vascular, peritoneal, cerebrospinal or, pleural cavities, etc.) and the assembly 10. Moreover, one or more optional flushing port 44 may be integrated along the assembly 10 to facilitate the cleaning of a clogged catheter 12; perforations in the lumen of the catheter facilitate in the flushing process.

FIGS. 6A-6C illustrate an example of how the tip 40 may be utilized for cleaning or clearing the sensor 30. As shown in FIG. 6A, sensor 30 may be contained within catheter 12 and proximal to tip 40. A blunt tip 50 of sensor 30 may be urged distally such that it is forced through valve tip 40, as shown in FIG. 6B, thereby cleaning the surface of the sensor 30 and allowing for the exposed sensor 30 to take a reading of the peritoneal fluid in proximity to the catheter 12. If either valve 40 or catheter 12 is occluded, a flushing port 44 may be used as well. Once the reading has been taken, sensor 30 may then retract proximally into catheter 12 past tip 40 which may again clean sensor 30 its shown in FIG. 6C. An inductive recharging coil 52 is also shown in this variation within assembly 10 for enabling the inductive charging of the device.

FIG. 7 illustrates another variation of a device utilizing a semi-permeable membrane 60 along the catheter body 12 and a curled, non-erosive tip 62. The semi-permeable membrane 60 may allow for long-term analyte and/or insulin diffusion through the membrane 60 and into the catheter for contact with the sensor 30 housed within without foreign body reaction or requirement for fluid infusion. The membrane 60 may allow for rapid diffusion utilizing materials, e.g., ePTFE, silicone lattice, etc. or coatings such as albumin, heparin, etc.

The curled tip 62 of the catheter is an example of an atraumatic feature that can prevent erosion or insult to tissue within the body cavity. In one embodiment, the atraumatic tip 62 may be tunneled to the site of implantation. Placement in the peritoneal cavity may involve dissection of the posterior rectus sheath from the peritoneum, angulation of the catheter downward into the true pelvis then perforation of the peritoneum to ensure downward angulation of the catheter into the pelvis. The proximal catheter may then be tunneled subcutaneously to the subcutaneous portion of the implant. In yet another embodiment, the distal end of the peritoneal catheter may be inserted into the peritoneal cavity then the tip of the catheter may be firmly attached to the parietal peritoneum or bladder with the sensor located proximal to the attached tip within the peritoneal cavity. The tip of the catheter may also exit the peritoneal cavity and be buried in the subcutaneous space leaving both ends of the catheter in the subcutaneous space with a short segment containing the sensor and/or infusion port exposed within the peritoneal cavity. This feature may prevent potential erosion of the tip of the catheter through visceral peritoneum into peritoneal structures and will maintain the catheter segment firmly and permanently away from the omentum and/mesentery. This type of catheter placement may be useful for any peritoneal catheter including peritoneal dialysis catheters to prevent complications and obstructions. If placed with laparoscopy, open surgery or percutaneously the omentum may also be tacked up away from the catheter during placement. The catheter may be placed without visualization or with visualization such as ultrasound visualization, laparoscopic visualization, or by other radiologic guidance.

Some embodiments of the technology advantageously include an inductive powering or charging circuit. In order to minimize the size of the implant and maximize its life, a small battery may be used that requires recharging on a daily, weekly, or monthly basis. Alternatively, the device may be externally powered by placement of an inductive coil over the device during operation, as shown above. Any of the features illustrated in any of the figures or described within this specification may be used alone or in conjunction with other features illustrated in each figure.

FIGS. 8-13 show aspects of the function and clinical use of a pre-peritoneal pocket formation tool to form a pocket in which to place the pre-peritoneal reservoir. FIG. 8 provides a schematic view of an implantation site pocket formation tool 70 at various stages of deployment.

FIGS. 9-14 show aspects of the function and clinical use of a pocket formation tool 70 to insert the pre-peritoneal reservoir of the catheter-based embodiment of the device. FIG. 9 shows an embodiment of the pocket formation tool 70 entering into the pre-peritoneal implantation site 72, the tool disposed in a compressed state within a tool insertion catheter.

Figure 10:
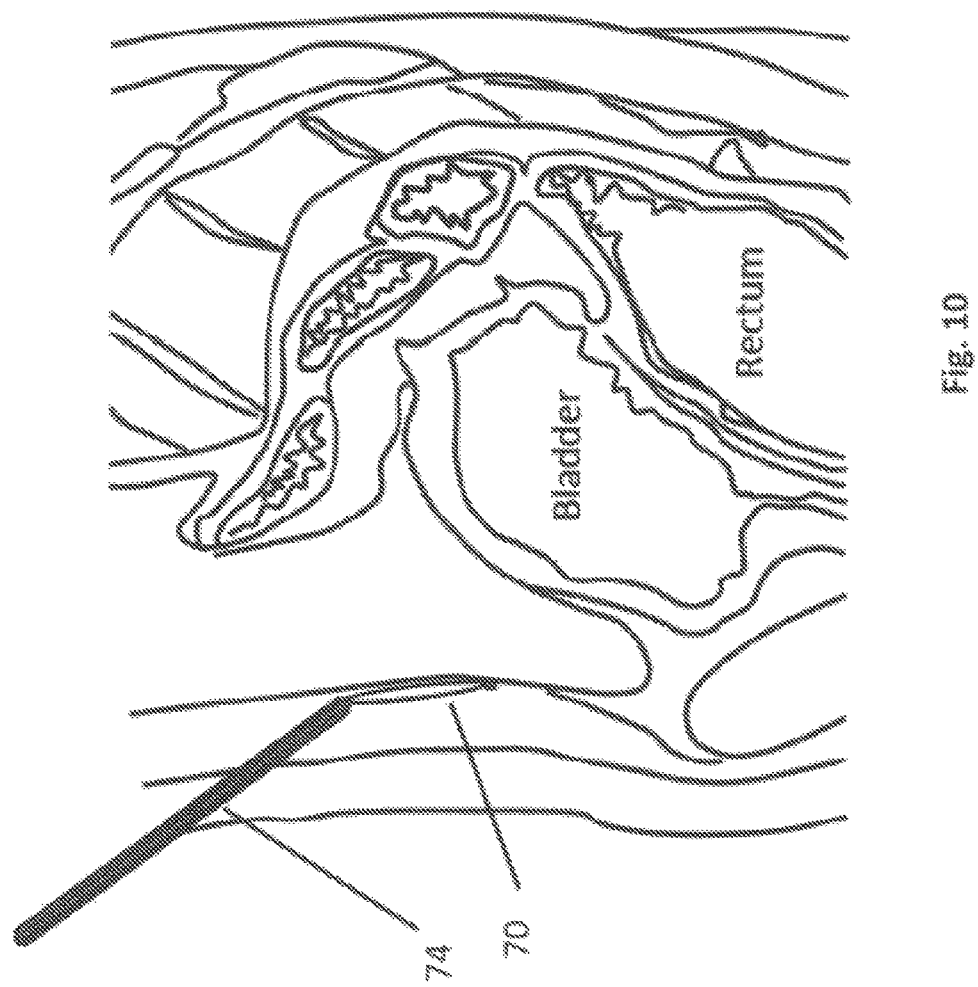
FIG. 10 shows the pocket formation tool having emerged from the tool insertion catheter, and having expanded, thereby formed an implantation site pocket at the preperitoneal site.
Figure 11:
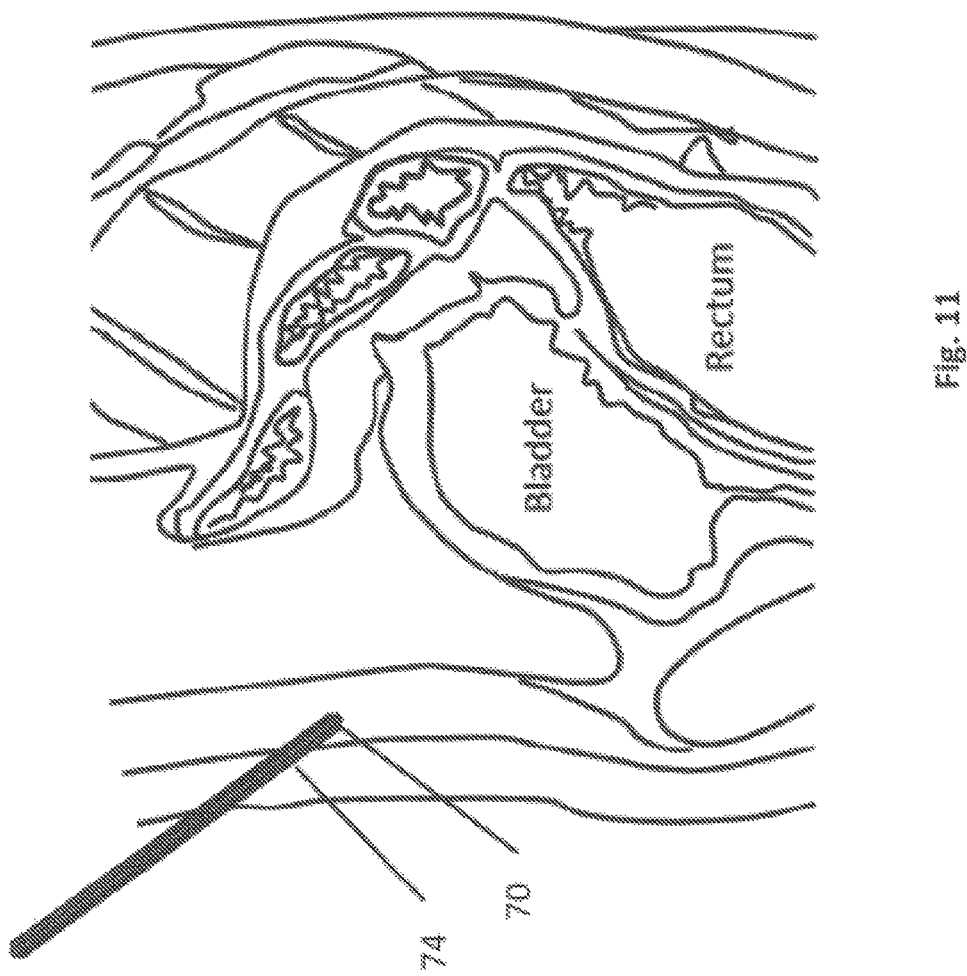
FIG. 11 shows the tool insertion catheter in place after the pocket formation tool has been withdrawn from the pocket site
Figure 12:
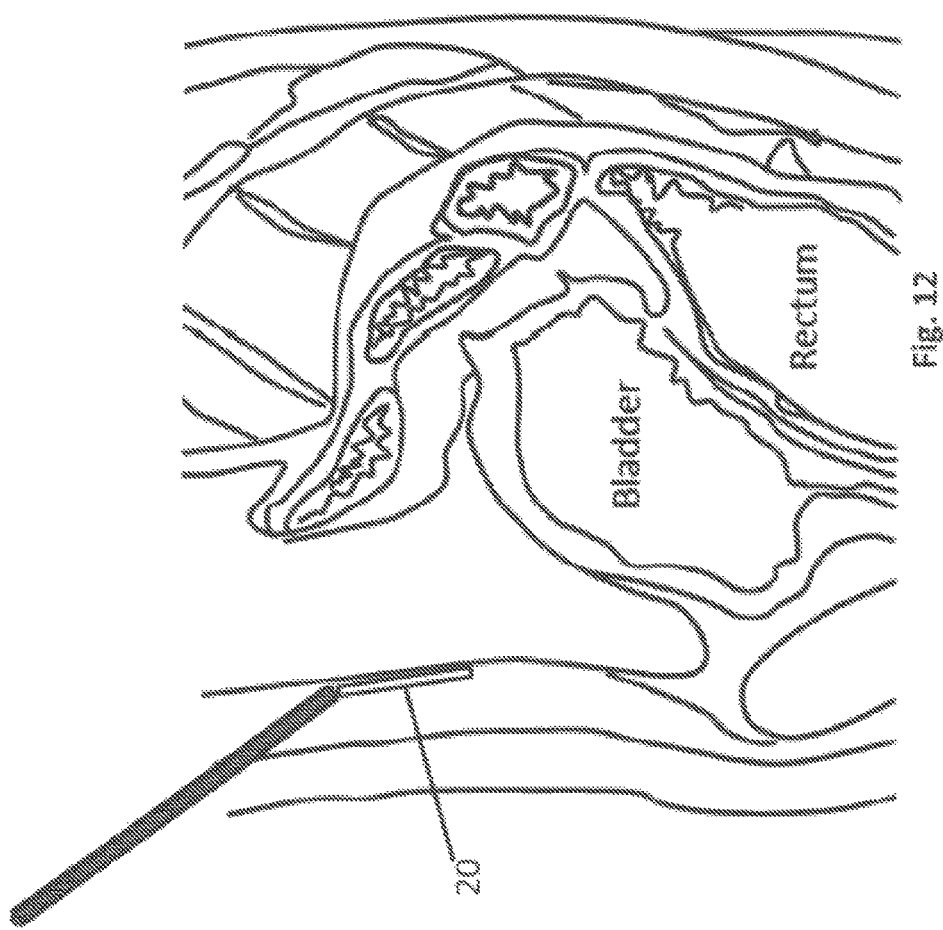
FIG. 12 shows a drug-dispensing reservoir in an early stage of deployment, as it emerges from the insertion catheter, into the implantation pocket.
Figure 13:
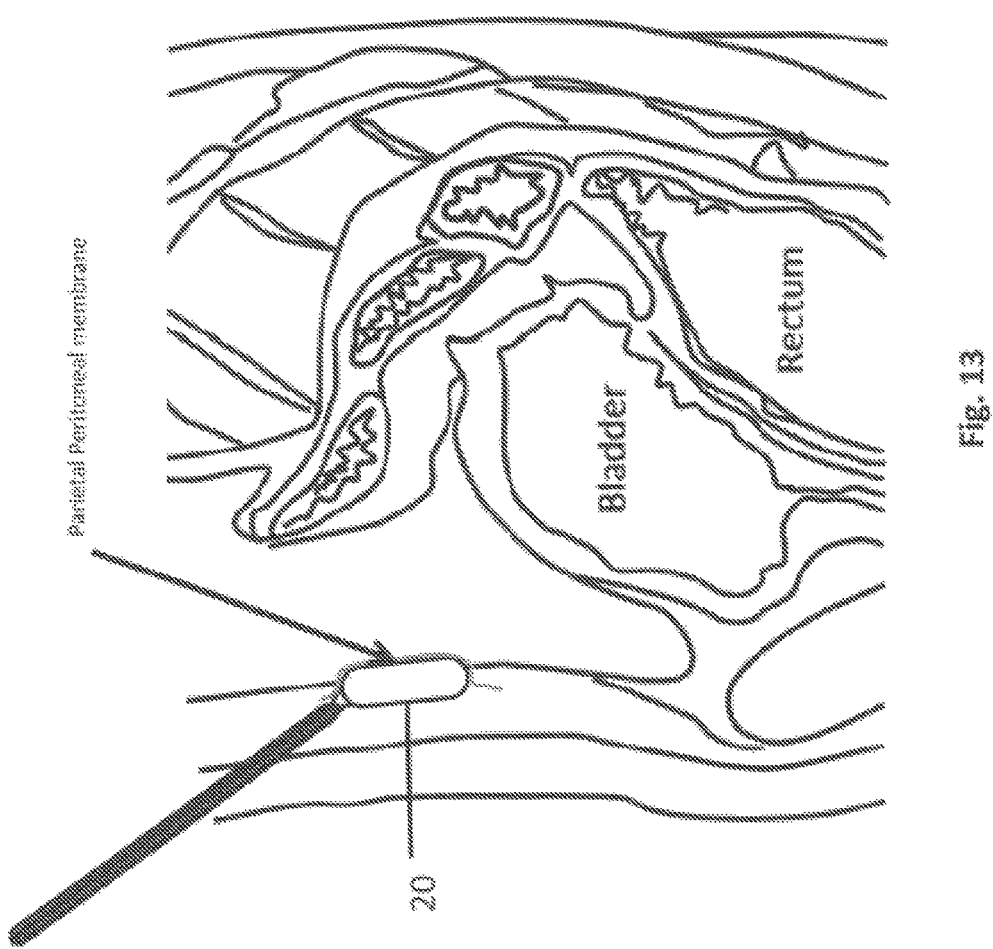
FIG. 13 shows a complete drug dispensing reservoir expanding as it emerges from the insertion catheter.

In FIGS. 10-11 a pocket formation tool 70 passes through the recurs muscles into the pre-peritoneal space while inside of a sheath 74, and expands to create a pocket. In FIG. 11, once the expansion process is finished the pocket formation tool is removed. FIGS. 12-13 show a minimally invasive placement of an infusion reservoir 20 through the same sheath and inflated inside of the pocket created by the tool. The infusion reservoir may be connected to a subcutaneous pump with outflow into any site within the body. In an alternative embodiment, the infusion reservoir may also be a rigid reservoir and inserted through a surgical incision.

Figure 14:
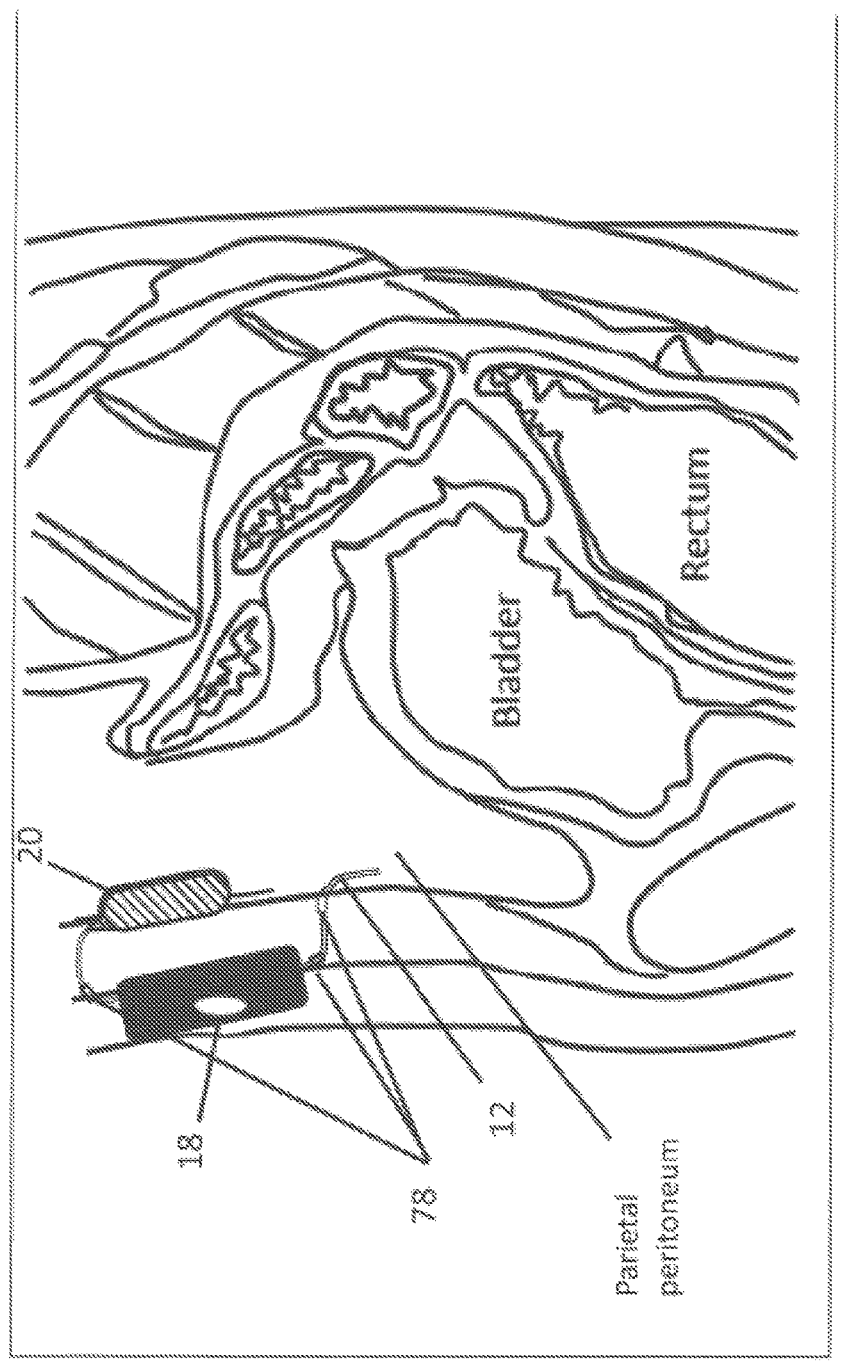
FIG. 14 shows a complete drug dispensing apparatus, comprising a reservoir, pump, and infusion catheter in place within the implantation pocket.

In FIG. 14 the sheath 74 has been removed and the catheter is attached to a pump that may or may not have a percutaneously accessible infusion port 18 to refill the pre-peritoneal reservoir. The reservoir may also be placed in a similar manner within the peritoneal cavity or in a submuscular space (to prevent cosmetic issues with its inflation). In the intraperitoneal embodiment, the distal end of the reservoir may be affixed to the peritoneal wall to prevent its interfering with normal bowel function. The reservoir 20 is preferably fabricated from a very strong, biocompatible material and, ideally, fiber-reinforced or reinforced with multiple layers. The reservoir itself must be able to withstand extreme forces without rupturing, including large pressures and force from a direct impact. The reservoir may also contain a neutralizing chemical in between the layers of the reservoir such that any rupture will expose the drug inside the reservoir to the neutralizing chemical (e.g., activated charcoal) within the pocket and prevent overdose. The reservoir may preferably be fabricated from silicone polyimide, polyurethane, PTFE, ePTFE or another strong, flexible, biocompatible material including composite materials for superior strength.

FIG. 14 shows the use of an embodiment of the reservoir 20 in conjunction with an embodiment of a peritoneal infusion port 18. One or more of the catheters, preferably both, may utilize an in-growth prevention cuff 78, such as a Dacron cuff, to prevent infection tracking subcutaneously or when exiting the peritoneal cavity. The outlet to the infusion pump may also lead to the subcutaneous, vascular, CST, pleural, intramuscular spaces or any other tissue or cavity within the body. In the illustrated embodiment, the peritoneal sampling catheter 12 is shown as a combination sensor, drug/fluid delivery conduit.

In the illustrated embodiment, the sensor may detect peritoneal glucose levels and the subcutaneous pump may automatically respond with an infusion of insulin into the peritoneal cavity if elevated glucose levels are detected. This insulin infusion may utilize the same conduit as the sensor or may enter the cavity at a different location in order to preserve the sensing function. In another embodiment the sensor may detect glucose levels in one anatomical space, while a subcutaneous pump may respond with an infusion of insulin in another anatomical space or tissue.

In particular embodiments, both the sensor and sampling catheter may be swept clean by the infusion of the insulin and/or the fluid flush. In yet another embodiment, the fluid path to reservoir and/or to the outlet catheter may be in communication with a pressure sensor. This pressure sensor may be used to monitor the status of the reservoir and, in certain instances, monitor the status of the patient as well. In the case of monitoring the reservoir, absence of the expected pressure profile during and between pumping sessions may trigger an alert that there is a clog in the lumen between the pump and the reservoir or between the pump and the outflow catheter. For example, algorithms can be developed to track the behavior of the sensor so that if signal decays, it can trigger an alert for a flush.

Figure 15:
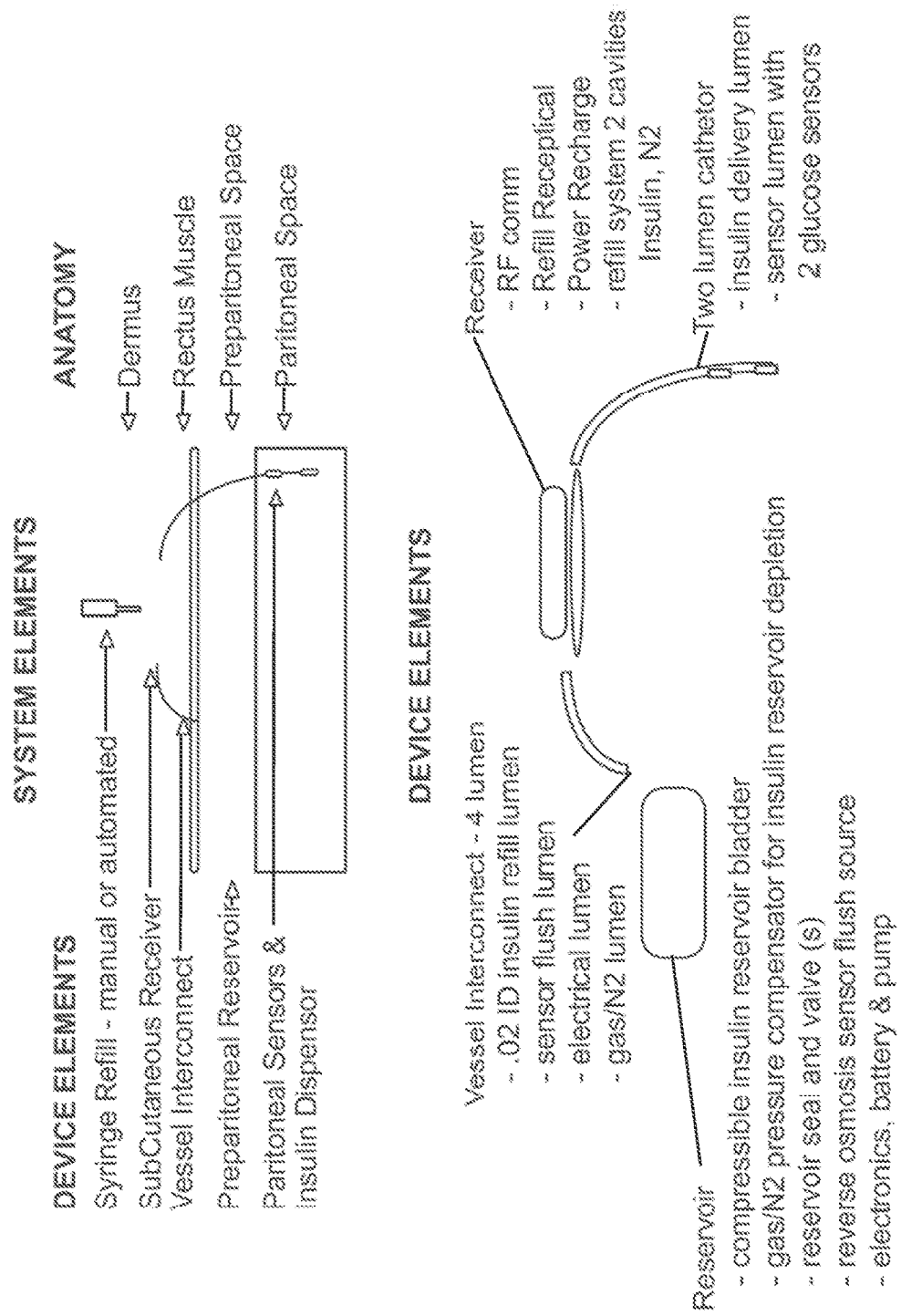
FIG. 15 shows schematic diagram of an embodiment of an implantable drug reservoir.

FIG. 15 shows a schematic representation of an embodiment of an implantable drug delivery reservoir.

Rapidly sampling pressure within a preperitoneal (or peritoneal) reservoir and using the correct algorithms for analysis enables easy detection of intraperitoneal pressure, heart rate, respiratory rate and relative cardiac output. The latter two often precede a crisis and may alert the user or healthcare provider that a patient is decompensating. Addition of a temperature sensor and/or pulse oximeter would allow for the continuous detection of patient status with this multi-functional implant. All embodiments may require intermittent transdermal recharging and/or battery replacement. In the event that the reservoir or other component of the device is used to monitor a patient's health status, the device could also be a passive implant that is inductively activated on an active implant that is inductively recharged. The monitoring implant may reside, in its entirety or in part, in the preperitoneal, subcutaneous, intramuscular or intra peritoneal space and be place with a simple percutaneous procedure. This implant may also have applicability in situations where it is imperative to remotely determine a user's health status (i.e., for soldiers in the military).

Alternatively, the catheter and/or device may be inserted into another space, e.g., subcutaneous, vascular, peritoneal, cerebrospinal, pleural spaces, etc. The percutaneous implant may also be placed in another cavity in order to simplify sensing. The peritoneal fluid which normally collects and/or flows through the peritoneal cavity may be detected by the catheter and analyzed via the device to detect the concentration of glucose within the fluid. The percutaneous catheter, in its ideal embodiment, may be placed within the body via a percutaneous, laparoscopic or interventional radiology procedure and chronically remain within the body. The sensor portion of the catheter may be replaced frequently (i.e. daily) or very infrequently (i.e. ever decade) or at any time point in between. Ideally the catheter will incorporate multiple sensors and sensors with different sensing modalities, for example, redundant subcutaneous sensors disclosed below, to provide orthogonal redundancy in the space that it is sensing (preferably the peritoneal cavity), The catheter may be used to infuse therapeutics, anti-thrombotics, fibrinolytics and may be intermittently sterilized on its inner and/or outer surface of its lumens once it is attached to the externalized artificial pancreas via an automated chemical, ultraviolet, mechanical, electrical or pharmaceutical intervention.

The glucose sensor(s) may utilize any one of a variety of modalities including, but not limited to, enzymatic sensors, photometric sensors, mid-infrared and near-infrared wavelength sensors, phosphorescent sensors, etc. More than one modality may be employed, as well, to ensure that results are accurate. The protective catheter and/or the sensor may also be replaced as needed or on a schedule.

The device may also incorporate a sterilizing and/or cleaning mechanism as described in patent application PCT/US2008/73279 entitled "METHOD AND APPARATUS FOR AUTOMATED ACTIVE STERILIZATION OF FULLY IMPLANTED DEVICES" and U.S. Prov. 60/964, 822 filed Aug. 15, 2007, each of which are herein incorporated by reference in their entirety.

Systems developed fir the sensing of interstitial glucose in the subcutaneous space in conjunction with an insulin pump have exhibited erratic night-time behavior including episodes of hypoglycemia and false reports of hypoglycemia. There have been several attempts to combat these issues, including taming the insulin pump off at night with resulting loss of control), adding redundant, co-located sensors to provide two signals (with the hope that only one will be deviant) and adding glucagon infusion to the insulin pump infusion circuit (which, in the instance of a false hypoglycemia would induce a real hyperglycemia). Therefore, in order to close the loop and have a glucose sensor that controls an insulin pump there exists a strong need for a more reliable means of detecting and reporting blood glucose.

One embodiment of the present invention may provide a more reliable means of detecting and reporting blood glucose by utilizing one or more redundant sensors that are not co-located. While this is not intuitive and far from ideal (it adds to the patient burden by requiring two separate placements of two separate devices) the research conducted by the inventors prior to this filing indicate that co-location, or even locating another sensor in the near proximity, will result in redundant signals that are both erroneous.

Figure 18:
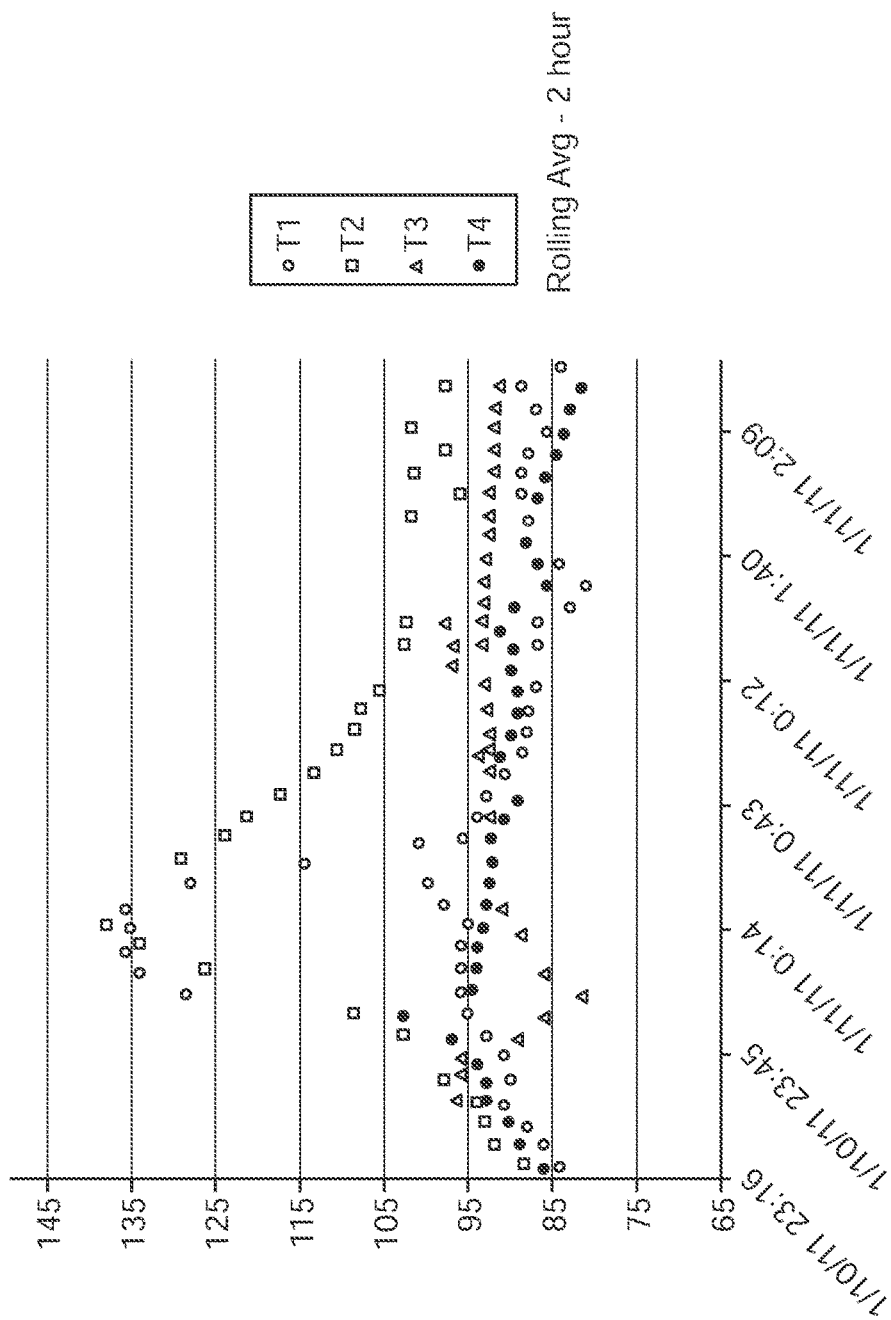
FIG. 18 shows a graphical representation of subcutaneous blood glucose and body position data recorded from a sleeping subject.
Figure 19:
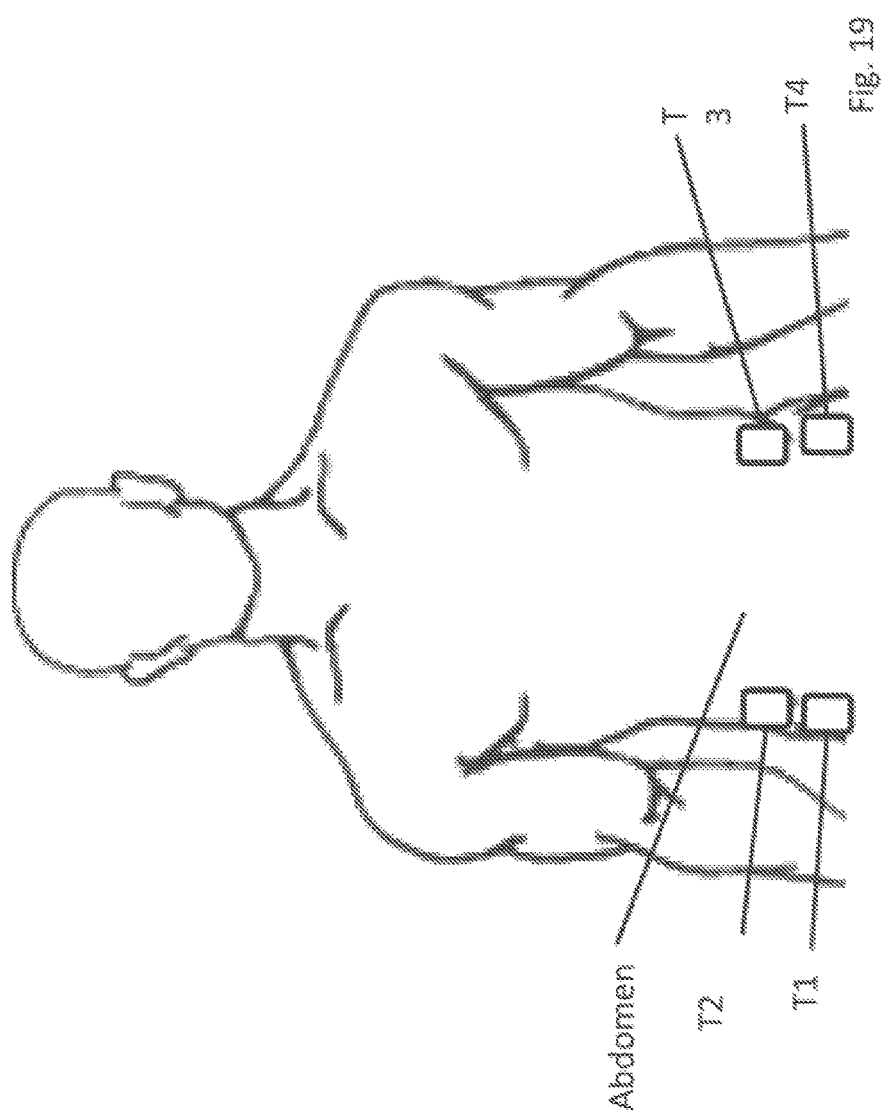
FIG. 19 shows the placement of four subcutaneous blood glucose sensors on a subject.

FIG. 18 is graphical representation of subcutaneous blood glucose and body position data recorded from a sleeping subject. As shown in FIG. 19, four subcutaneous blood glucose sensors were used, two placed on each flank of a subject. The dip in blood glucose shown in the tracing below details that both sensors T1 and T2 (located ~2 inches apart on the same flank) resulted in an erroneous reading while the subject was documented to have been sleeping on them.

The data graphed above (which is just a sample of the voluminous data that have been acquired) demonstrate that the use of co-located (or even near proximity) sensors in the subcutaneous space would not provide the added safety that one would expect. In fact, if the two co-located sensors T1 and T2 above were considered to have been accurate, this subject would have received a dose of insulin to bring them down 50 mg/dL (from 135 mg/dL) when they would have actually been at 90 mg/dL and the result would have been profound, dangerous hypoglycemia and, potentially, death.

In order to provide a signal from a subcutaneous sensor that is reliable enough that insulin may be dosed off of the reading without user intervention (ie a fully-closed loop), the inventors have found that the sensors absolutely must be placed on surfaces that would not be expected to be compressed or otherwise locally pressurized at the same time. The sensors could then be queried and, in the event of a large deviation in the signal, the system may be programmed to recognize the correct signal or the user may be asked to verify that the change in blood glucose is real. In both cases, the algorithm may use the "safest" signal (ie the one that would not dose insulin) in the event of a disparity between the two readings.

Alternatively, the cutaneous or subcutaneous portion of the sensor or transmitter may either be attached to or incorporate a sensor (pressure, force, temperature, etc.). Information from the thermometer, pressure and/or force transducer may be used to determine when the readings from the sensor may not be trusted (ie when there is excessive pressure or when temperature is too high or low). The sensor data may be transmitted to the receiver and/or insulin pump (in a closed-loop system) but no action will be taken (by the patient or the dosed loop pump) in the setting of a sensor reading indicating that the subcutaneous sensor is in the presence of excessive pressure and/or temperature. The pressure sensor may be incorporated within the device or may be art additional device with its own ability to communicate wirelessly with the meter and/or transmitter.

Figure 20:
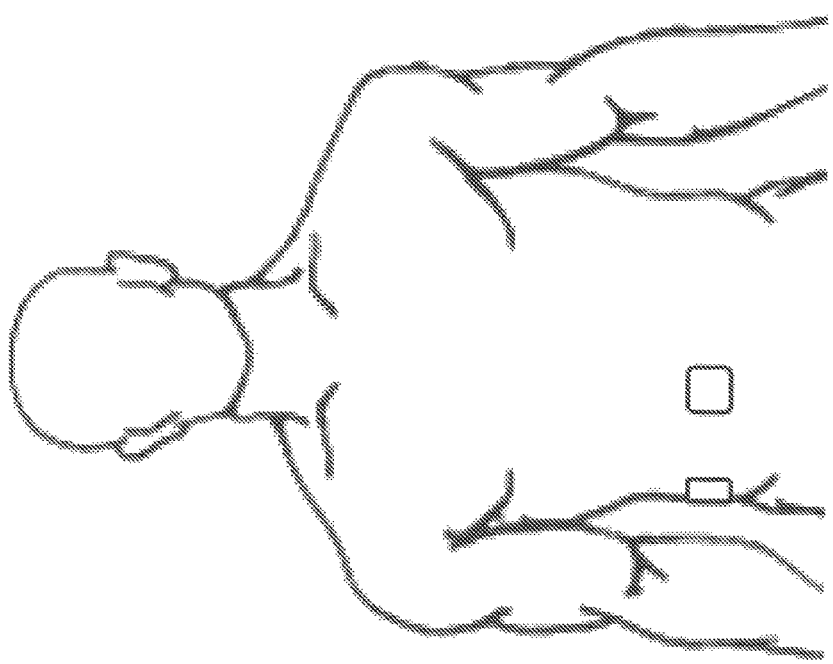
FIGS. 20-22 show examples of safe, redundant placements of sensors.
Figure 21:
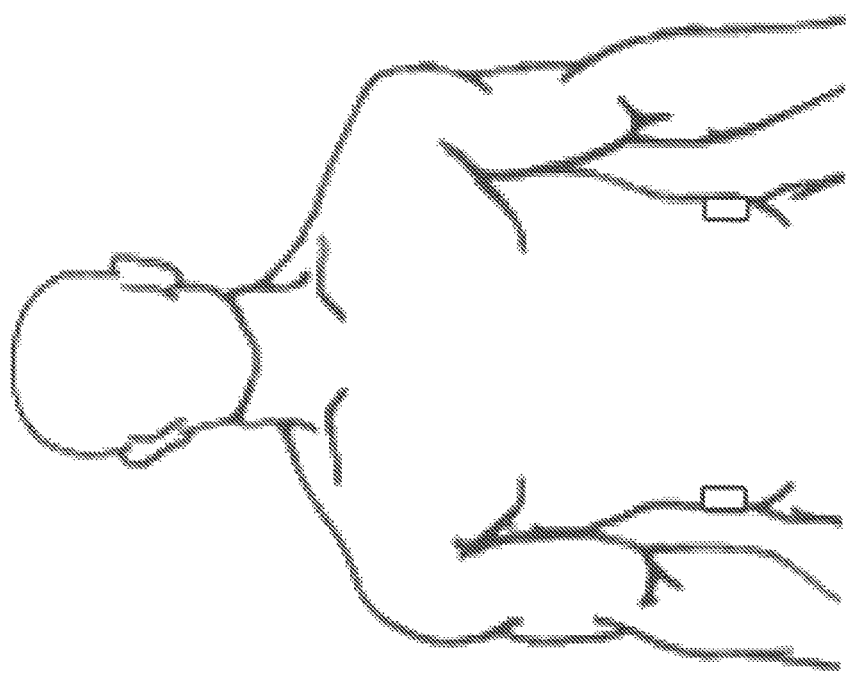
Figure 22:
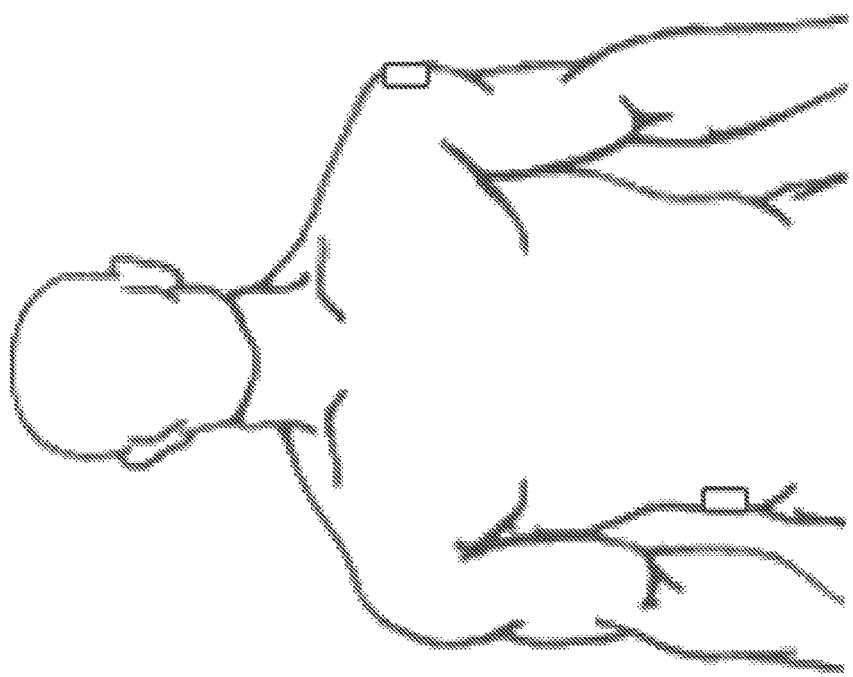

FIGS. 20-22 show examples of safe, redundant placements of sensors.

The present invention may take a variety of embodiments with the only requisite feature being that of a placement in two, disparate regions of the body. In FIG. 19, the setup is detailed wherein it was determined by the inventor that co-located sensors (or sensors located in the same proximity) would not provide a safe redundancy.

FIG. 20 illustrates the minimum separation that would be allowable in order to provide a safe redundancy. Even with this separation, some parallel deviation of sensors is possible due to the blood supply for the tissues originating from the same source (same half of the body). Ideally a positioning scheme more like that of FIG. 21 or FIG. 22 would be utilized wherein the sensors are on either side of the midline and not so close as to allow them to be simultaneously compressed (ie not one on either side of the umbilicus wherein a belly sleeper could easily compress both at the same time).

FIG. 21 illustrates an ideal separation of redundant sensors in that simultaneous direct compression of the sensors would be very unlikely (if not impossible) and the sensors receive blood flow from different halves of the body.

FIG. 22 illustrates another safe redundancy in that the arm and abdomen perfusion have quite different vasculature and the positioning on opposite sides of the body helps ensure that simultaneous local compression would not be an issue.

Figure 25:
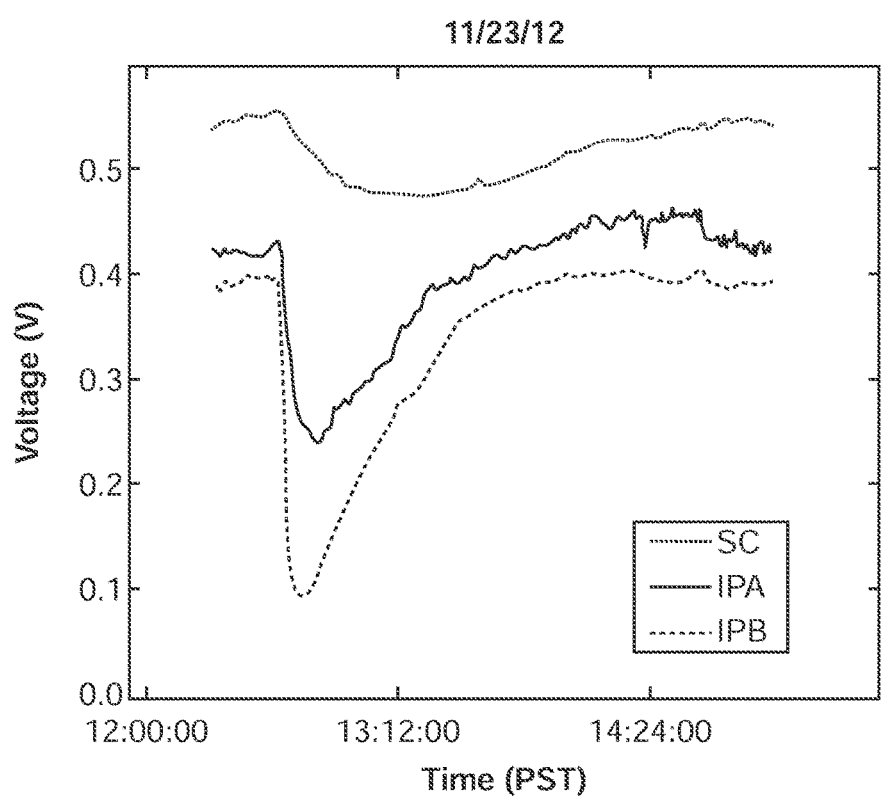
FIGS. 25-28 show graphical representations of glucose level data from a sheep implanted with three glucose-sensing catheters at three, nine, fourteen, and seventeen days post-implantation.

FIG. 25 shows a graphical representation of glucose level data from a sheep implanted with three glucose-sensing catheters at three days post-implantation. Each catheter used two glucose sensors for redundancy. They were all capable of flushing in order to remove tissue encapsulation, and were flushed regularly for the first two days after implantation. Two of the catheters were implanted intraperitoneally (IPA and IPB), and one was implanted subcutaneously (SC). An intravenous glucose tolerance test (IVGTT) was administered by in 0.5 mg/kg of D50 (50% dextrose) solution into the sheep's jugular vein. Data were collected once per minute and the two readings from each sensor were averaged to give a single reading for each catheter. Sensor voltages represented glucose levels, with lower voltages indicating higher glucose levels. The peritoneal response was much more rapid than the subcutaneous response, indicating that peritoneal kinetics are superior.

Figure 26:
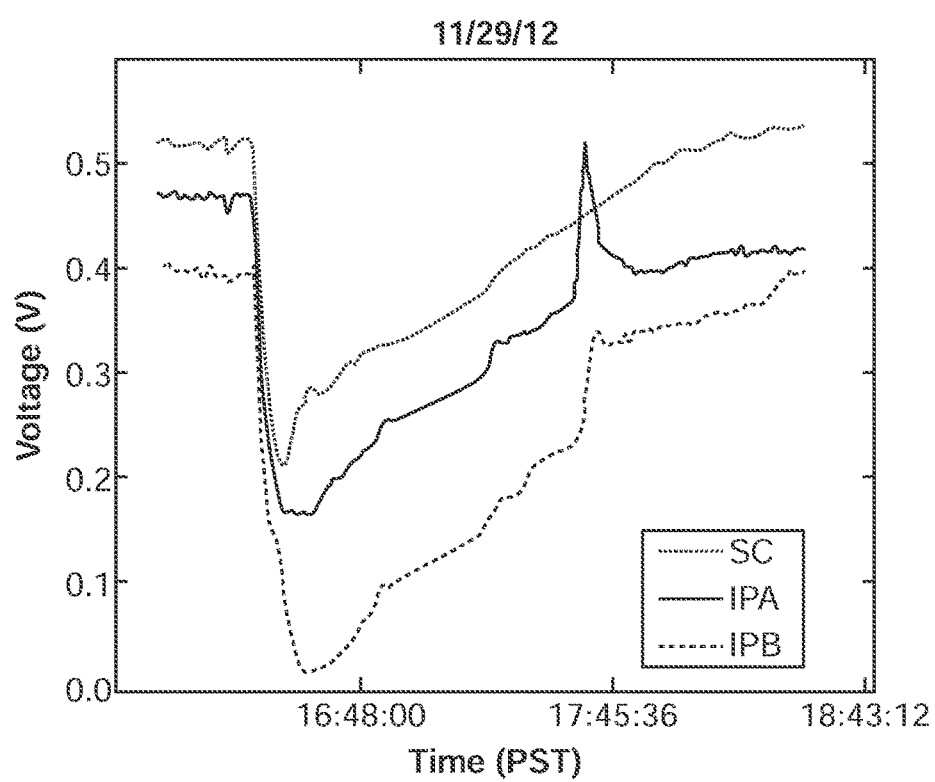

FIG. 26 shows a graphical representation of glucose level data from a sheep implanted with three glucose-sensing catheters at nine days post-implantation. An IVGTT of 0.5 mg/kg D50 was performed. By this point, the sensors had begun to become encapsulated. The encapsulation of the subcutaneous sensor was fairly vascular, which led to improved Hood flow to the sensor and an improvement in response time. Both peritoneal sensors continued to maintain fast response times. Near the end of the challenge, catheter IPA was flushed to remove tissue encapsulation, as shown by the sudden spike in voltage (the voltage of IPB was also affected, due to its close proximity to IPA, but its encapsulation was left intact).

Figure 27:
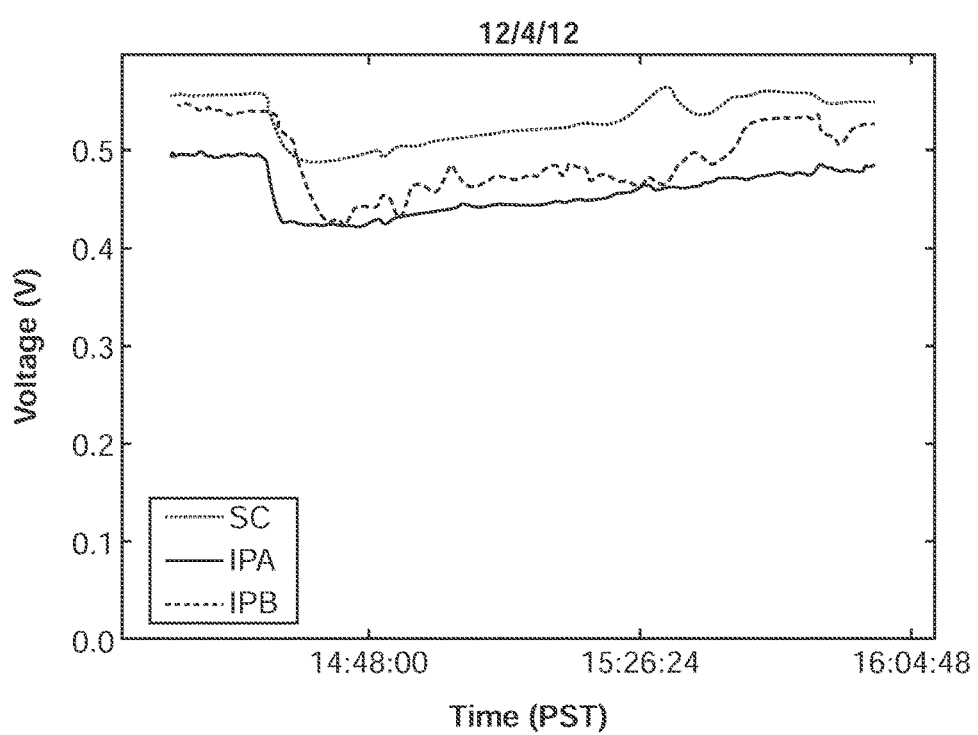

FIG. 27 shows a graphical representation of glucose level data from a sheep implanted with three glucose-sensing catheters at fourteen days post-implantation. An IVGTT of 0.167 mg/kg of D50 was performed. Catheter IPB had a delayed response, due to the continued encapsulation of its sensors. Catheter IPA maintained a fast response time, as did the subcutaneous catheter. However, the initial slope of the subcutaneous response began to show signs of flattening, indicating that its encapsulation had become more fibrous and less vascular.

Figure 28:
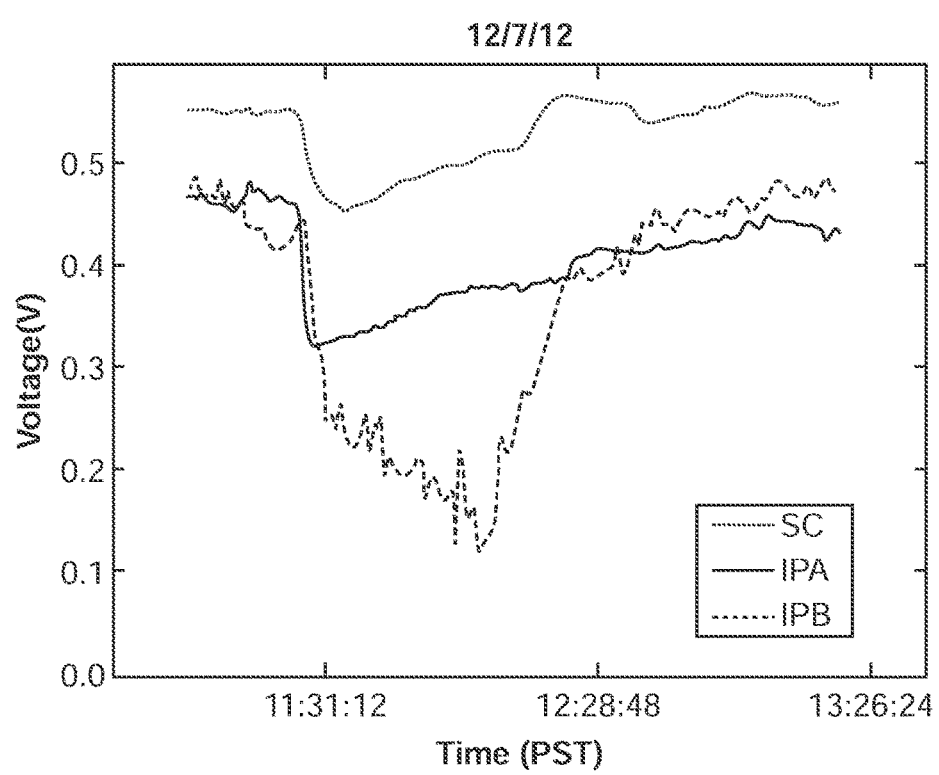

FIG. 28 shows a graphical representation of glucose level data from a sheep implanted with three glucose-sensing catheters at seventeen days post-implantation. An IVGTT of 0.25 mg/kg of D50 was performed. Catheter IPB continued to take longer than the other catheters to reach its minimum voltage, due to further thickening of its encapsulation. Its response had also become increasingly noisy. Once again, catheter IPA maintained a fast response time. Catheter SC also responded quickly, but continued to show signs of fibrous encapsulation, reaching its minimum voltage later than catheter IPA. At the end of the challenge, catheter IPA was flushed again to remove tissue encapsulation.

Figure 23:
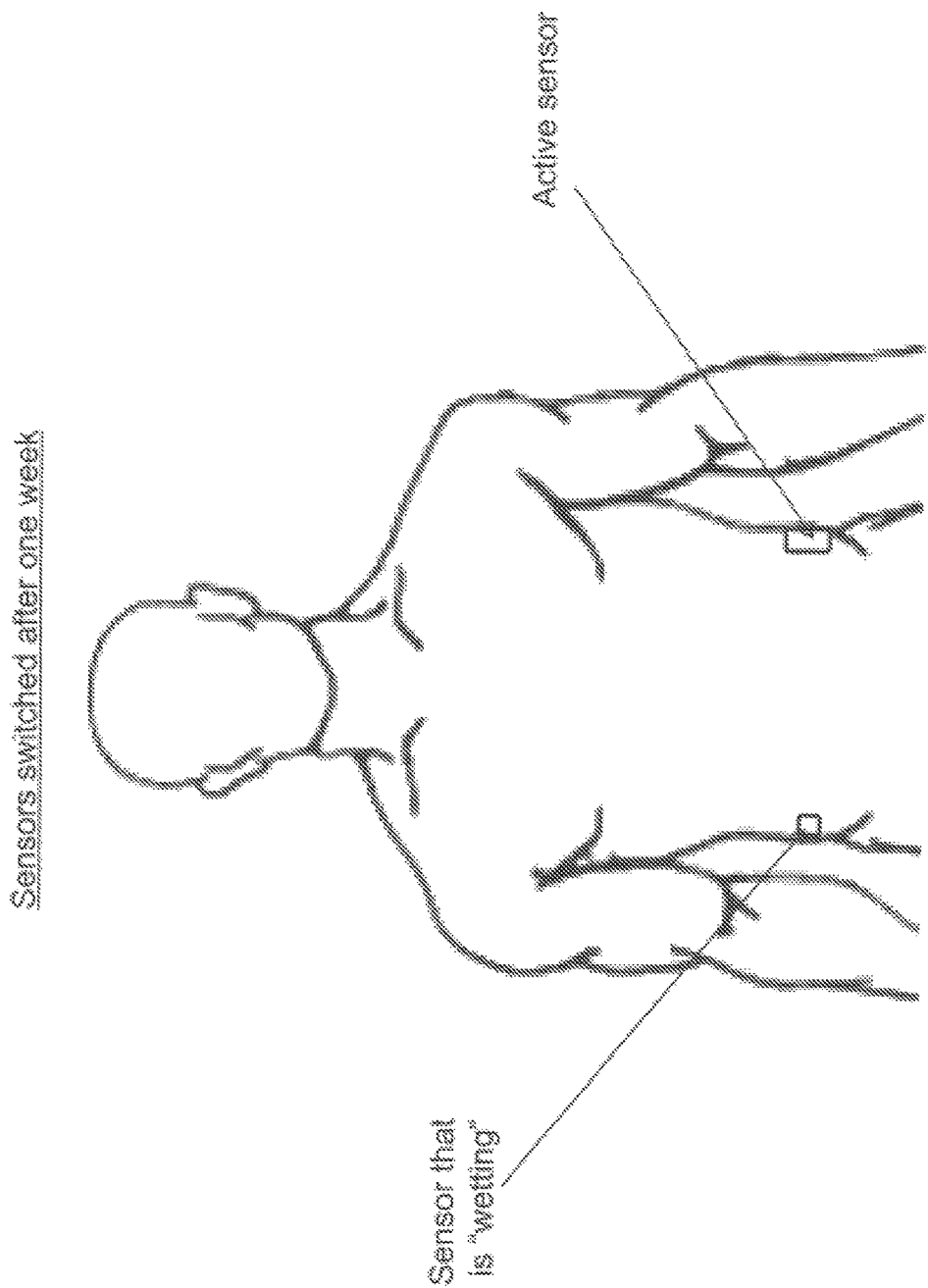
FIGS. 23-24 shows two or more sensors that are separated both spatially and temporally
Figure 24:
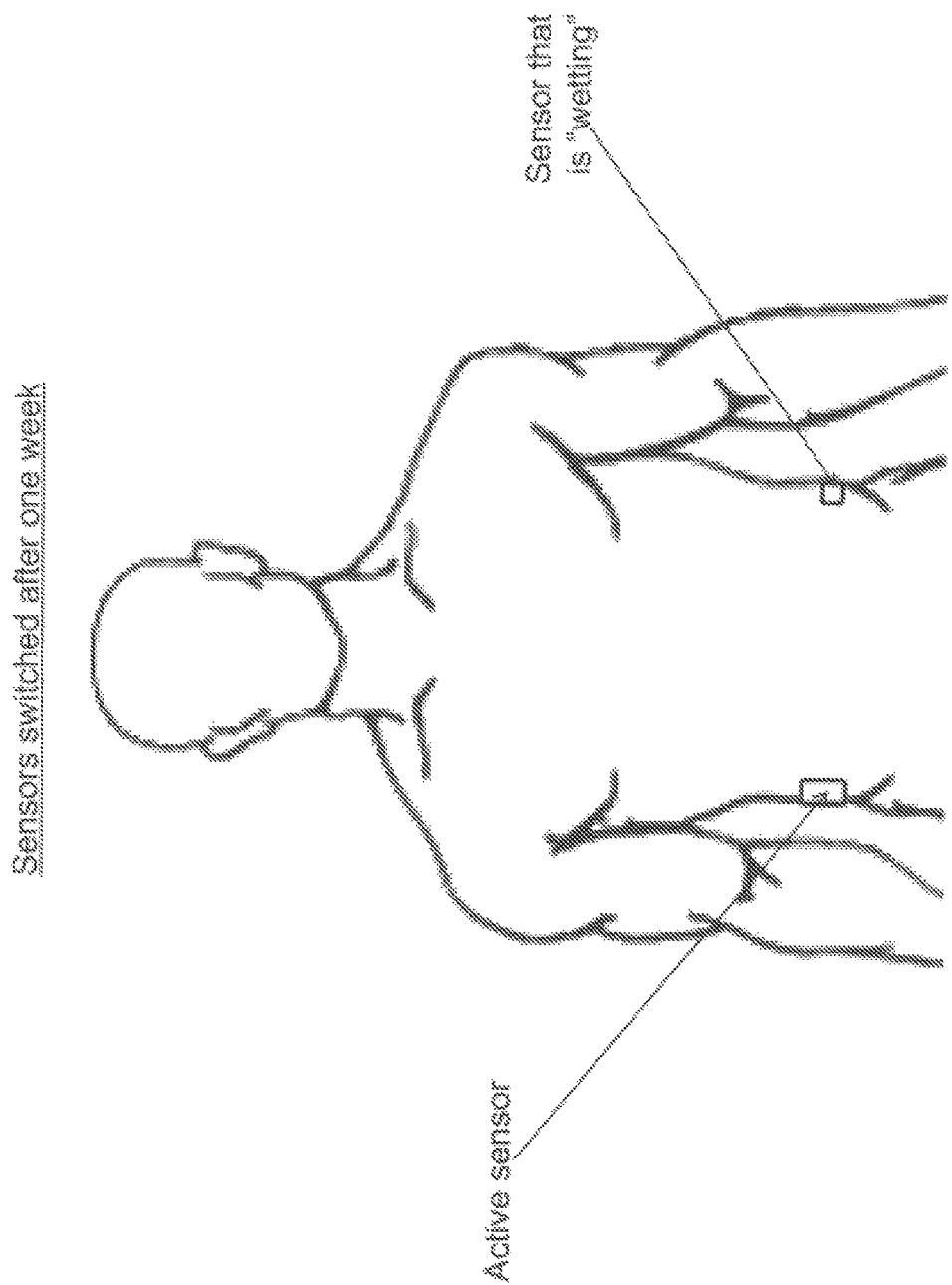

As shown in FIGS. 23-24, the present invention, preferably, employs two or more sensors that are separated both spatially (such that they will generate their own capsular response) and temporally (such that one of the sensors is always in the sweet spot zone of 7-21 days in vivo). The inventors have discovered that the response to the sensor is what, in fact, makes it respond more readily. This angiogenic response (i.e. proliferation of blood vessels) creates a heavily vascularized capsule starting after day 5. The blood vessels then start to recede after week 3 as they are replaced by a fibrous capsule. Thus, to ensure optimal performance one or more sensors must always be surrounded by this vascularized capsule. In order to ensure this, in the preferred embodiment one sensor is placed every 7-10 days and the signal from the newest sensor (still in its first week) is used simply as a safety backup to the older sensor within its vascularized capsule. This algorithm providing for the differential handling of the readings (i.e. prioritization of the readings from the older sensor) from each sensor based on its time in vivo is novel and not contemplated elsewhere in the prior art. Each of the two sensors may be placed as infrequently as every 10 days (to maximize cost-efficacy) and each sensor placement may be in and of itself redundant (i.e. two sensors placed at a time so that these readings may also have spatial redundancy if not temporal).

Figure 16:
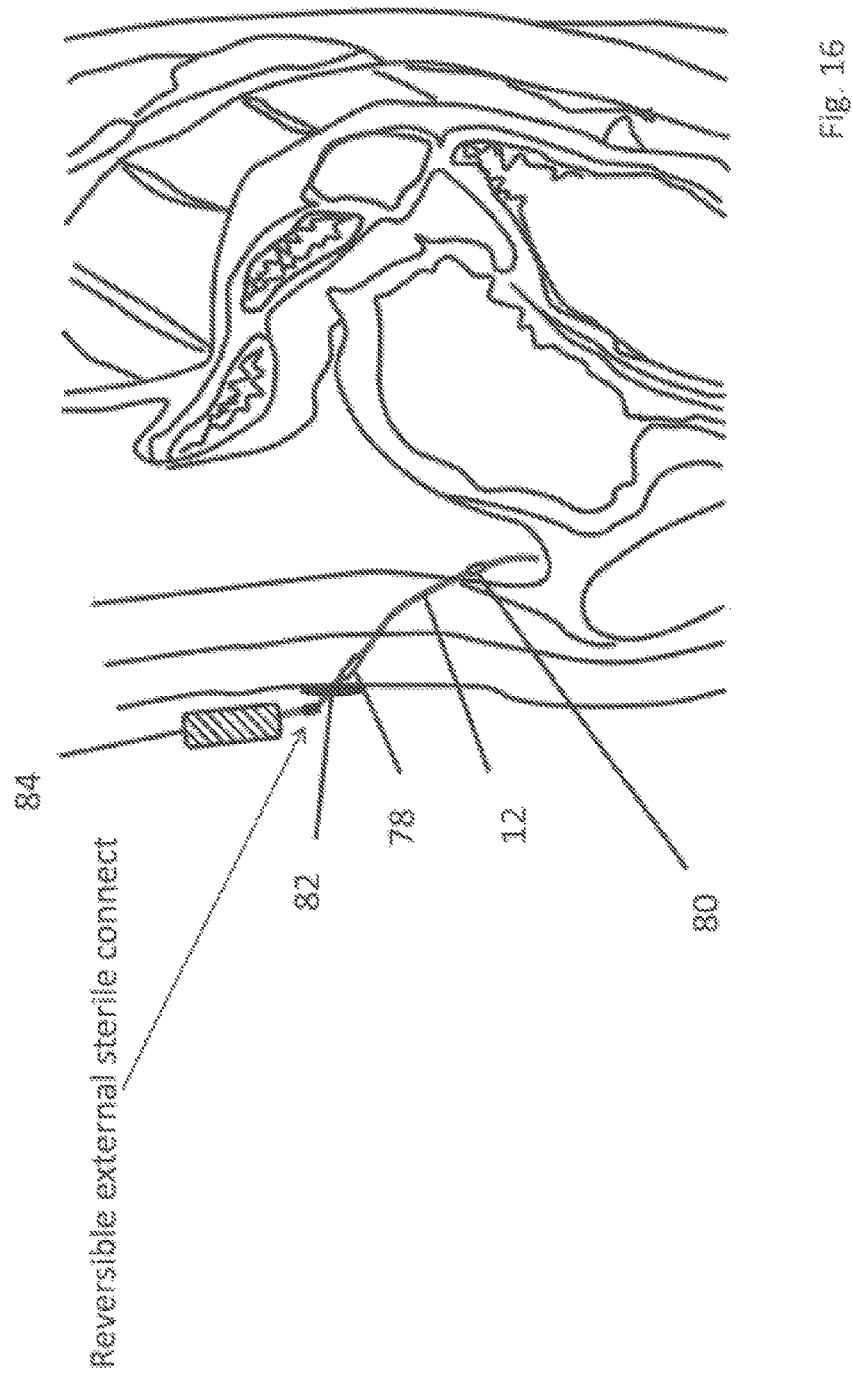
FIG. 16 illustrates an example for external placement of the sensing/infusion catheter embodiment of the device.

FIG. 16 illustrates one example for placement of the glucose sensing system or artificial pancreas electronic unit on the abdominal surface of subject. It may, alternatively, be placed anywhere on the surface including the thorax, back, buttocks, etc. The external glucose sensor and/or insulin pump 84 preferably utilizes a multi-lumen infusion/sensing catheter which may be placed, preferably, in the true pelvis. The insertion procedure for this catheter may also be accompanied by either laparoscopic rectus sheath tunneling or omentectomy/tacking of the omentum. The external electronics/artificial pancreas may automatically back flush this catheter intermittently to maintain flow or backflushing may require a manual intervention. The catheter may, preferably, have one or more anti-adhesive or ingrowth cuffs 78. Desirably, a silicone ring (not shown) around the anti-adhesion cuffs 80 separating the sensing catheter and the anti-adhesion cuff prevents tissue growth under the anti-adhesion cuff. The catheter may incorporate an infusion lumen (i.e. insulin) and analyte (i.e. glucose) sensor. In function, the catheter will be attached to an external glucose monitor and/or insulin pump (artificial pancreas). The external controller may also contain agitating mechanism and/or sensor cleaning mechanism and may reversibly connect to catheter and may be disposable or reusable. The external glucose monitor and/or insulin pump may consist of one (artificial pancreas) or two (insulin pump and separate glucose sensor) devices providing closed loop feedback with peritoneal glucose sensing and peritoneal insulin delivery. A skin site protector 82 protects the incision site on the surface of the skin.

Figure 17:
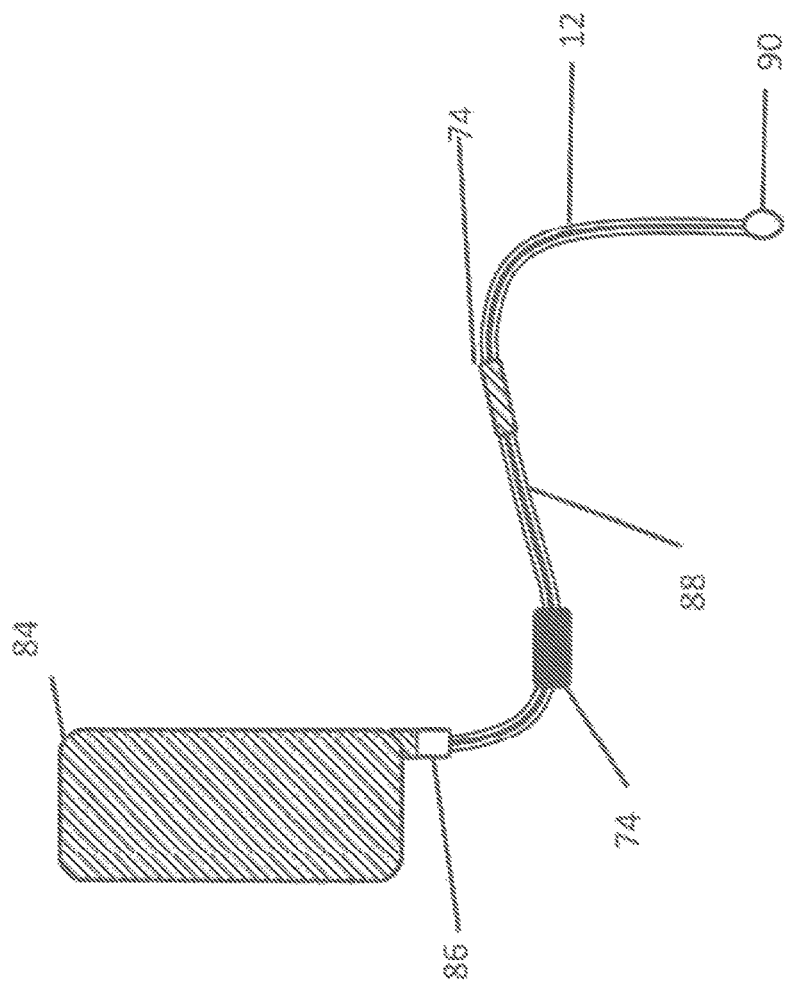
FIG. 17 shows an example of an externally-placed sensing/infusion catheter embodiment.

FIG. 17 shows an example of an externally placed sensing/infusion catheter embodiment. The external controller may, preferably, be reversibly attachable to the implanted catheter 12. Optionally, one or more drugs or other active agents may be incorporated into the catheter, e.g., to prevent clogging and/or preventing infection. The glucose sensor(s) may travel alongside or be within the insulin infusion sheath 88. Ideally the sensors will be distant from the insulin infusion site to prevent interference with the glucose reading. Fluid may also be circulated through the multi-lumen catheter (or single lumen catheter with intermittent flow (in then out) and drawn in over the sensor within the pump. The pump may be able to clean sensor or catheter via direct mechanical removal of any film or ultrasound or agitation, for example. The sensor may be anywhere along or within the catheter and preferably at the blunt tip 90 of catheter. One or more optional anti-fibrin/anti-adhesion cuff may be employed to ensure that any fibrin sheath distal to cuff is swept away with fluid infusion (insulin or catheter flush solution such as normal saline, heparin). Catheter may include sterilization elements (such as electric current, silver, ultraviolet radiation, etc.) and may, preferably, connect to externalized pump. One or more subcutaneous ingrowth cuffs may be employed to prevent tracking of any infection or fluid along catheter.

Alternatively, the glucose sensor (e.g., an optical sensor) may be positioned within the protective catheter. While the sensor is in electrical or wireless communication with the assembly through the catheter, the sensor may be positioned near or at a distal opening of the catheter. Thus, fluid may be circulated through the catheter which may comprise a multi-lumen or single lumen catheter. The catheter allows for intermittent flow (e.g., in then out) of fluid drawn in over the sensor and within an optional pump within the assembly. Such a pump may urge fluid through the catheter to clean the sensor or catheter via direct mechanical removal of any film or ultrasound or agitation for example. The pump may be configured to intermittently reverse direction to ensure lumen patency.

In its ideal embodiment, the glucose sensor may be integrated or affixed to the exterior surface of the catheter itself in order to minimize fluid accumulation and lag in any potential space. This applies to enzymatic, optical and chemical sensors, all of which would benefit from direct connection to peritoneal fluid without fluid pooling. In its ideal embodiment, as well, small, smooth rounded perforations or apertures will be present distal to the anti-adhesion cuff and in proximity to the sensor. Intermittent flushing of this lumen, then, would eject fluid from these perforations and "sweep" any accumulated debris or fibrin sheath from the catheter into the peritoneum for reabsorption. The anti-adhesion cuff may be used, in this instance, to provide a programmed area of fibrin sheath weakness so that it can be detached from the catheter in a controlled manner. As long as the flushing is relatively frequent the volume of the infusion need not be large since the fibrin sheath will be in its thin, wispy state until a minimum of 30 days have passed. Alternatively, the flush need not be automated and may instead be programmed to flush only once a capsule has been detected (by lag time, optical sensing, etc.). Ideally, in its preferred embodiment as well, the flush itself will be programmed on a frequent basis, though, and will allow for automated calibration of the sensor. In this instance the flush may consist of a calibrated glucose-containing solution that is ejected into the cavity, sweeping away any capsule and triggering the sensor to calibrate to that know concentration. Due to the sensitivity surrounding hypoglycemic episodes the solution could be an 80 mg/dL solution of glucose or could, preferably, be two or three alternating concentrations of glucose that the external (or internal) pump draws from and signals to the sensor to calibrate to that concentration. The pump may then be refilled with the flush at the time of insulin refill. In this external embodiment (peritoneal insulin infusing catheter and peritoneal glucose sensor traveling across the skin and outside of the body), the flush need not be concentrated and can be greater in volume than previously disclosed implanted versions of this device allowing for more flexibility in catheter maintenance. In addition, the external version of this device, while increasing the infection risk associated with an externalized catheter, may also incorporate more powerful sterilization techniques to prevent infection. For example, power limitations are much less of an issue for an externalized device where replacing and recharging the battery is not an issue. Use of ultraviolet radiation during insulin and flush infusion, then, is a viable option to ensure complete sterility of any fluid inflow. Other sterilization modalities mentioned above and in cross-referenced filings disclose alternative methods of sterilization of both the inner and outer walls of the infusion/sensing catheter to ensure that infection does not occur.

In its ideal embodiment, the catheter of shown in FIG. 16 and 17 may have certain components replaced (i.e. the sensor) with a simple, sterile removal and insertion procedure without the requirement for a new puncture or incision (i.e. it slides right out of the infusion/sensing catheter and is replaced in the same manner). The catheter may also reversibly attach the external electronic component of the device allowing for this element to be replaced, recharged, refilled, etc. while another fully recharged and refilled external unit is attached in a sterile manner. In its ideal embodiment the external unit incorporates an automated sterilization procedure during detachment and/or reattachment at the site of the connector.

Any of these designs may also be employed with a fully implantable pump design so long as the peritoneal cavity is used for sensing and delivery. Additionally and/or alternatively, the sensor may be moved relative to the catheter (e.g., slide out of the assembly and/or catheter or rotate within the assembly or catheter. The catheter may alternatively remain stationary its position and instead be cleaned using ultrasound, fluid lavage, etc. In this and other embodiments, one or more flushing ports or reservoirs may be incorporated to provide for cleaning of the system in the event that the system is not in direct contact with the fluid it needs to take its readings.

Example A outlines an exemplary research strategy to test the safety and efficacy of the pre-peritoneal reservoir.

EXAMPLE A

Pre-Peritoneal Reservoir Research Strategy

Type I diabetes mellitus (T1DM) is associated with numerous complications including blindness, renal failure, painful nerve disorders, and amputation. In addition to its devastating toll in human suffering, T1DM and its complications result in significant health care expenditures for families and constitute a major societal economic burden. Clinical trials have demonstrated significant reductions in complications of T1DM through intensive control of blood glucose levels. Thus, patients with T1DM are expected to experience dramatic improvements in their quality of life and life expectancy when the goal of engineering an artificial pancreas is finally realized.

One component of the artificial pancreas is the ability to deliver insulin to the bloodstream reliably, safely, and durably. We have designed a peritoneal insulin delivery system which takes advantage of the proven-safe components of prior designs, then builds on these by incorporating redundant fail-safes for critical failure modes. Additionally, our design features a large pre-peritoneal insulin reservoir which confers significant advantages to the patient. The objective of this application is to establish the efficacy and safety of our approach. We will do this by validating performance and fail-safe characteristics at the bench and in a subacute and chronic pig model. Particular emphasis will be placed on ensuring that failure modes will be both rare and contained.

This contribution may enable closed-loop artificial pancreas systems to function autonomously for several mouths at a time between insulin refilling visits Additional advantages of the pre-peritoneal location of the reservoir, as compared to subcutaneous, are that it is protected from blunt trauma by the abdominal wall and is a more comfortable location for the patient. The larger reservoir may also enable the use of this system in insulin-resistant (T2DM) patients in whom large daily dosages of insulin are required.

Innovation

Figure 29:
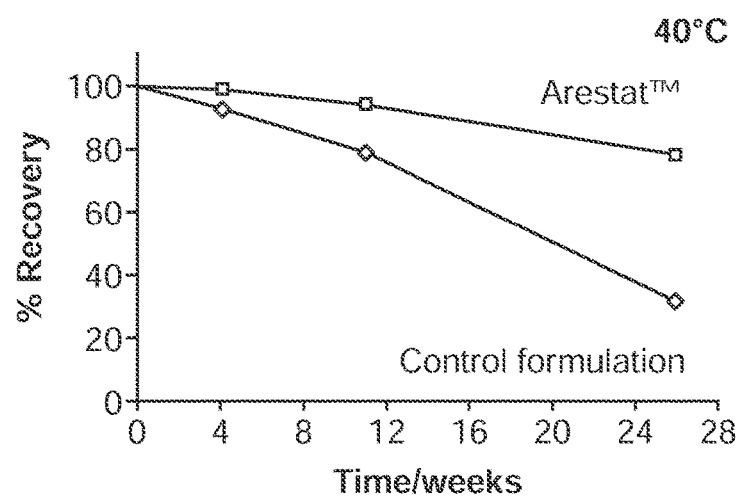
FIG. 29 shows the recovery of intact insulin following incubation at 40° C. in the control formulation of an insulin analogue and in the stabilized (Arestat™) formulation.

Fully implantable technologies for the insulin-delivery limb of the artificial pancreas have been successfully developed, tested, and used clinically with excellent safety profiles (1, 2). The Medtronic-Minimed (Northridge, Calif.) MIP2007 device features a subcutaneous reservoir, a pump, and tubing, which delivers insulin to the peritoneal space where it is rapidly absorbed, Despite its effectiveness, its production was discontinued due to problems associated with the very concentrated U400 insulin (Insuplant, made by Aventis) that it required due to the reservoir's small volume. A small reservoir was needed because of its subcutaneous location—larger-volumed reservoirs in this space are prone to eroding, through the skin. This location also results in some discomfort to the patient and susceptibility to blunt trauma. Using U100 in a small reservoir requires prohibitively frequent refills, incurring inconvenience and procedural risk to the patient. FIG. 29 shows the recovery of intact insulin following incubation at 40° C. in the control formulation of an insulin analogue and in the stabilized (Arestat™) formulation.

Our technology improves upon the Medtronic device by relocating the insulin reservoir component to the pre-peritoneal space. This design allows a reservoir with a much larger insulin capacity while maintaining the convenience of a subcutaneous refilling, recharging, and communication port. The larger reservoir enables the use of less-concentrated insulin with a substantially decreased risk of fibrillation (3). Our approach is complemented by emerging developments in soluble protein-stabilization formulations that extend the effective life of insulin and insulin analogues by several months (see FIG. 29). The pre-peritoneal reservoir design is also complementary to peritoneal sensing technologies under development which promise to improve the kinetics of continuous glucose monitoring and to resist tissue encapsulation. Together, these technologies enable the development of closed-loop artificial pancreas solutions which may safely function autonomously for several times longer than systems made from existing elements.

The concept behind our insulin-delivery strategy is relatively simple and uses existing technologies for implementation. First we describe what function each element performs and how the system elements work together. Then we address the potential failure modes of the device and the system design mitigations which minimize failure risk and ensure that if a failure does occur, the system "fails safe" in a way that prevents harm to the patient. Finally, we describe our approach to testing these risk mitigations.

Figure 30:
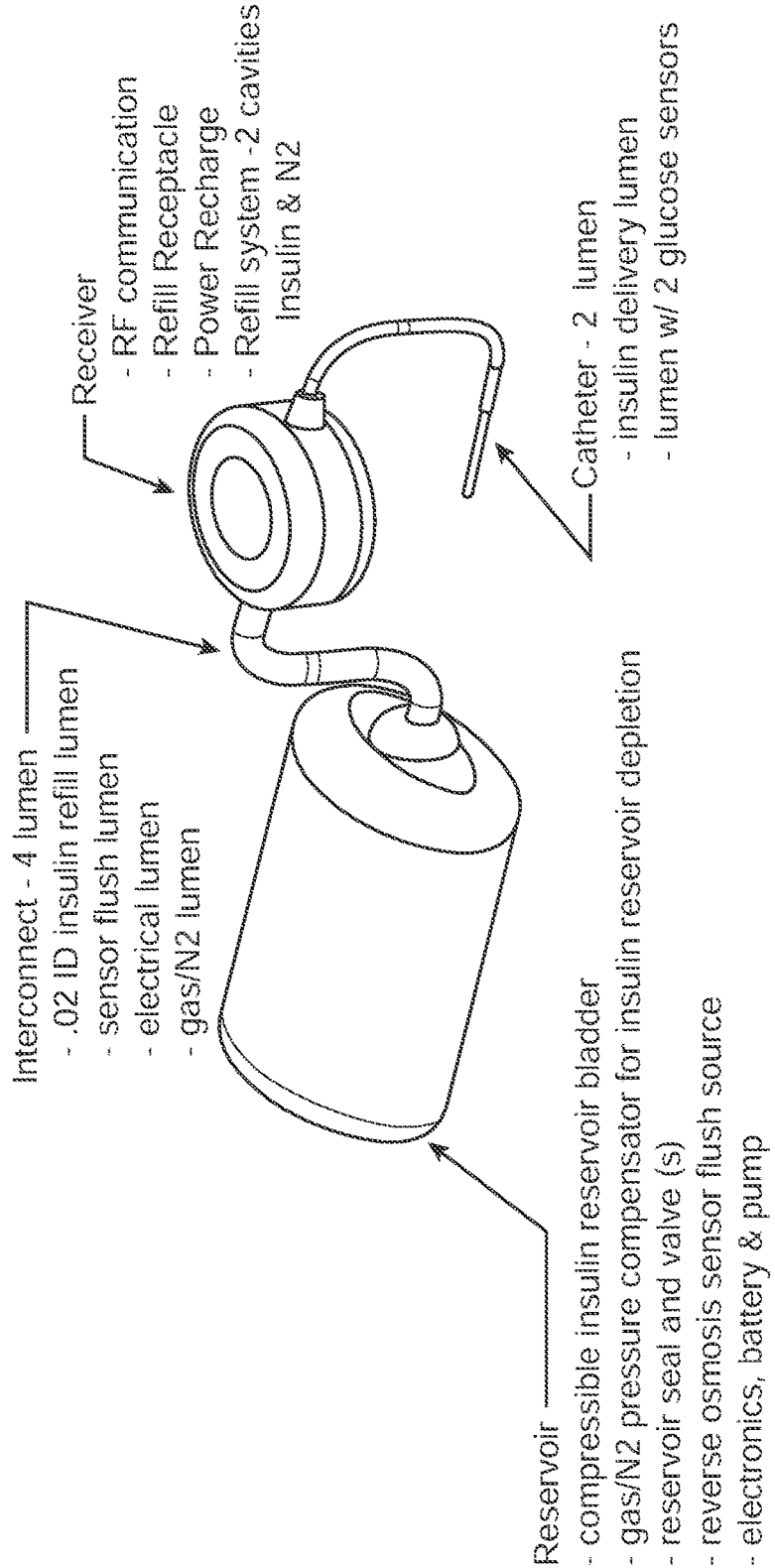
FIG. 30 illustrates Theranova's fully-implantable peritoneal insulin infusion pump design.
Figure 31:
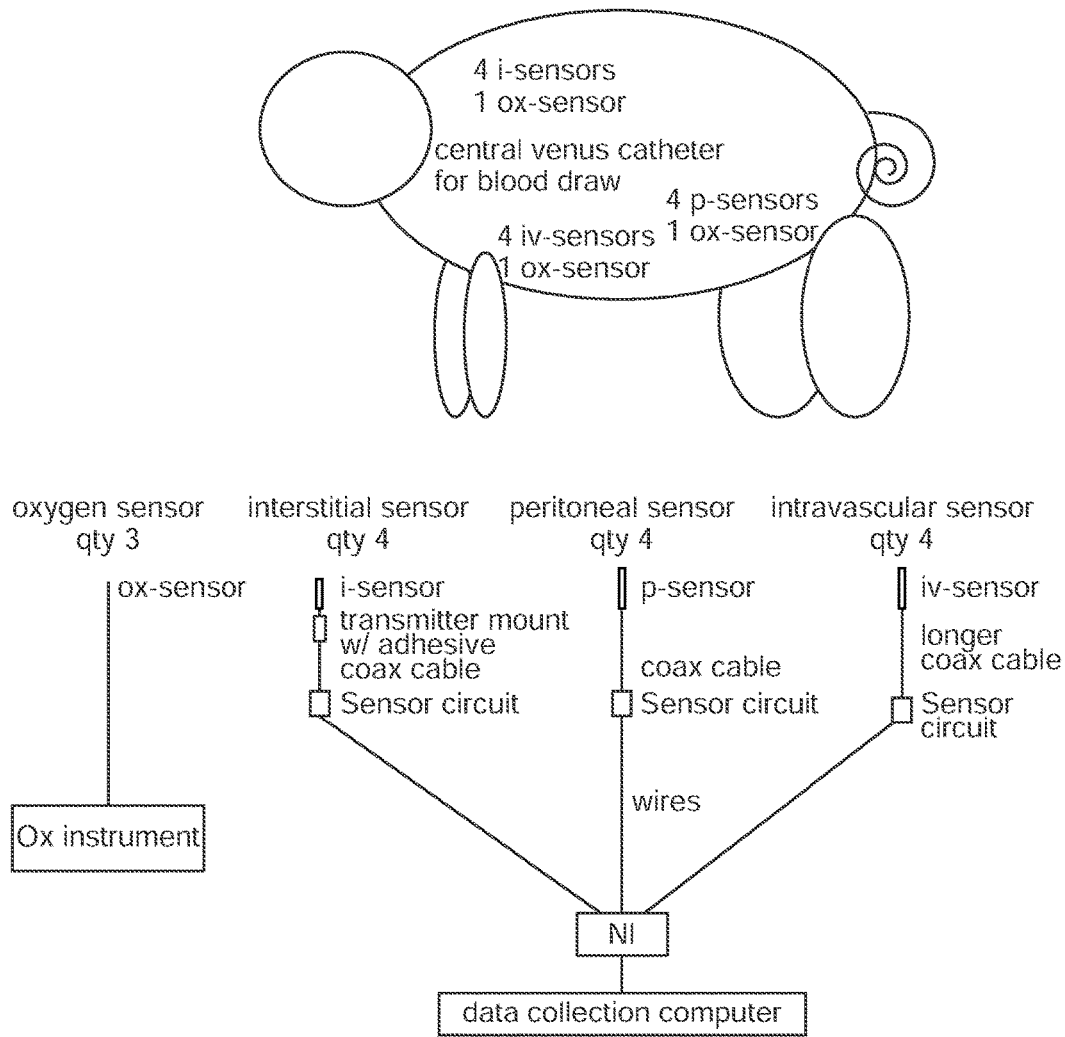
FIG. 31 shows a schematic representation of the instrumented acute animal study configuration

FIG. 30 illustrates a fully-implantable peritoneal insulin infusion pump design. This fully implantable system comprises 1) a pre-peritoneal reservoir, 2) a subcutaneous receiver with refill septum, 3) a reservoir-to-receiver interconnect and 4) an infusion catheter.

Reservoir. Situated in the pre-peritoneal space, this 200 cc Reservoir houses the components found in commercially available implantable pumps as well as some unique features, including a) a piston-pump insulin reservoir encased in titanium near a hermetic outer-housing with sealed bladder inside, b) a gas/$N_2$ pressure compensator to accommodate insulin reservoir volume depletion, and c) system electronics to include power, pump motor, RF, digital circuitry, redundant pressure sensors, redundant independently activated solenoid valves and other electronics required to accurately release precise doses of insulin. The reservoir also incorporates redundant pressure sensors in communication with the infusion Catheter so that any potential blockage of the infusion lumen will be rapidly reported. As with the Minimed device, the reservoir will be maintained under vacuum to ensure that insulin will not be released unintentionally.

Receiver. Situated in the subcutaneous space, this 20 cc Receiver houses the a) insulin, refill receptacle with docking septum, b) N evacuation chamber, c) RF communication antenna, and d) power induction/recharge receiver. The Receiver also incorporates a network of electrical fibers on its casing to allow for detection of impedance in the implant pocket to alert the user to a potential insulin escape.

Interconnect. This four-lumen, 7-cm-long conduit provides the physical connection between the Reservoir and Receiver. The four lumens include a) a 0.020" inner-diameter peritoneal insulin delivery lumen which passes through the receiver into the peritoneal cavity, b) an electrical power & signal-interconnects lumen c) a 0.020" inner-diameter insulin-refill lumen, and d) a 0.020" inner-diameter gas/$N_2$ evacuation lumen. The insulin refill lumen and gas/$N_2$ evacuation lumen are both accessible percutaneously via the Injector through a silicone septum in the Receiver.

Catheter. This 12-cm-long, 0.020" inner-diameter Catheter delivers the insulin to the peritoneal space. Insulin is pumped from the Reservoir travels through the Receiver and exits the distal end into the peritoneal cavity. The Catheter is fitted with strain reliefs at every juncture and is a single, continuous catheter from the Reservoir to the peritoneal cavity (it is simply potted into the Receiver). While the small lumen size requires additional energy to pump the insulin into the peritoneal cavity, it also provides an essential safeguard in that complete failure and disconnection of the lumen followed by immediate complete purging of its contents will result in a small enough dosing of insulin to be safe.

Injector (External Accessory). This external automated syringe is for refilling the Receiver with insulin and evacuating $N_2$ gas. Prior to any infusion of insulin into the reservoir, there must first be recognition of the Injector by the Receiver an electronic "handshake"). This handshake ensures that the primary lumen of the injector is seated into the insulin refill chamber in communication with the 0.020" insulin refill lumen and that a secondary lumen within the injector is mated with a small chamber in communication with the $N_2$ gas chamber at the opposite side of the piston pump in the Reservoir. Once the Injector and the implantable electronics perform their handshake, the impedance-sensing fibers on the outside of the Receiver are activated and U-100 Arestat-stabilized insulin is infused into the Reservoir while gas is evacuated. The refill process takes 60 minutes during which any insulin escape from the Receiver will be rapidly detected and reported to the user (see below).

External RF Communication and implant cell recharging (External Accessory). This handheld device will communicate wirelessly with the implant system to report insulin dosing history and system status including: notifications, battery charge status, insulin levels, and predicted days to refill. The recharging system will couple with the implant inductively to recharge the battery.

Following implantation, the patient will use a hat held communicator to dose their insulin as they would with a standard external insulin pump, The system includes an external battery-recharging accessory that the patient will use to recharge the implant on a monthly basis. The patient will align the external recharging belt over the subcutaneous Receiver and wear the belt for a minimum of 6 hours to provide a full recharge. For the typical T1DM patient the insulin reservoir is expected to require a ~yearly refill using the proprietary Injector. This estimate is based on a system capacity of 20,000 units, a daily requirement of 40-50 units (4, 5), and allowing for some insulin degradation. The system is designed for a 5-year life under normal operating conditions. This device will comply with ISO standards and in particular ISO 14708-1 and 14708-4.

Use of dispensing control valves in series, embedded within the reservoir, will ensure no leakage of insulin from the dispensing port under normal use. The Reservoir body itself consists of a stainless steel cavity under vacuum within a rigid titanium near-hermetic outer housing with sealed bladder to ensure that the Reservoir itself will not be a point of failure. Interconnects are double-layered and include strain relief. Furthermore, use of a small infusion catheter with an inner diameter of 0.020" ensures that even if the catheter were to become detached and empty its entire contents into the implant pocket, the dose would be tolerable and not cause life-threatening hypoglycemia. Despite these mitigations, the need to protect against inappropriate insulin release is very important; thus we will further mitigate this risk with a proprietary impedance-based insulin sensor on the outside of the Reservoir and Receiver. The automated detection of inappropriately released insulin will trigger a lockdown of all valves and sound an alarm for the patient, signaling them to take sugar and come to the clinic or emergency room.

Refill failure risks is one that has not been adequately addressed by current designs. In fact, there have been reports in the literature of failures with refill that resulted in dumping into the implant pocket (6). In order to avoid this, we have designed a custom Injector that interfaces with the refill septum in the Receiver. The Injector is disabled and unable to dispense insulin until it receives an electronic "handshake" from the device. This handshake is only provided once the refill needle is situated in the correct position across the septum aligning the insulin refill lumen and the gas evacuation lumen with their respective access lines. Once this has occurred the refill is enabled and the Injector slowly dispenses its contents into the reservoir while gas is evacuated. The Pump monitors the refill progress and reports any flagging in flow rates or change in impedance outside of the Receiver. These safeguards ensure that each Refill procedure will be completed safely in a controlled manner.

Improper dosing of insulin can take one of three forms: excessive delivery of insulin, inadequate delivery of insulin or deactivation of insulin.

Excessive Delivery of Insulin. This is a previously mitigated risk. This failure mode may be associated with actual reservoir rupture or catheter dislocation as discussed above. Excessive delivery of insulin during normal use is prevented by a variety of safeguards that are already commonly found in implantable pumps, including: redundant independent valves which must communicate synchronously to allow for any dosing, use of a high-resolution/micro-dosing pump to ensure very high resolution for each dose and delivery of insulin in small fractional series doses (fractional dosing).

Inadequate Dosing of Insulin. This is a risk that has not been adequately addressed by current designs. For example, one recent study found that it took >24 hours for the insulin pump to report that it had failed and was no longer delivering insulin (7). Redundant pressure sensors located prior to the redundant reservoir valves have been incorporated into our design in order to provide immediate feedback if there is a sustained pressure spike in the Infusion Catheter that would require further investigation.

Deactivation of Implanted Insulin. This is a risk that has not been adequately addressed by current designs. In fact, current insulin and insulin analogue formulations have been found to decay at body temperature such that the most stable of formulations decays to 80% functionality at 3 months and drops below 50% at 6 months. Due to this limitation, there has been no incentive to implant a larger reservoir to decrease the frequency of device refills. With the Arestat-stabilized insulin formulations, though, activity levels of 80% at 6 months have been achieved. We intend to evaluate the extent to which this stabilization increases the active life of insulin in vitro and then in vivo.

The implantation procedure will employ standard surgical techniques used widely in patients. A location will be identified for the subcutaneous refill port in the left or right suprailiac area. After an incision is made, a subcutaneous pocket will be formed for the refill port and implantation sites will be identified for both the pump/reservoir and the infusion catheter. A pre-peritoneal pocket will then be formed for the pump/reservoir after which it will be slipped into its pocket. The infusion catheter will then be tunneled into the true pelvis within the peritoneal cavity through the preformed subcutaneous pocket. The true pelvis is a site that has inherent resistance to encapsulation as demonstrated by the <5% incidence of mechanical obstruction (over 2 years) of peritoneal dialysis catheters implanted in this location (8). Finally, the subcutaneous refill port will be slipped into its pocket and stitched into place to prevent dislocation, and multi-layer closures of the abdominal wall will be performed.

Tissue Reaction. This is a risk that has been partially mitigated by similar designs. After implantation, the foreign body response will create a fibrotic pocket around the implant. While this is particularly true of the subcutaneous space, it is not the case with potential spaces such as the peritoneal cavity. In fact, Medtronic's peritoneal insulin pump proved to be capable of delivering accurate insulin doses to the peritoneal cavity in patients for several years. In one study of 63 patients implanted with this device, investigators noted the excellent resistance to encapsulation with their report of a median operation-free period of 78 months in patients implanted after 2000 (9). We intend to evaluate the extent to which our current device design will encourage healthy encapsulation of the pre-pertioneal and subcutaneous components without causing damage to adjacent tissues.

Bleeding. This is a previously mitigated risk. One issue that has arisen in the pre-peritoneal space is the potential for difficulty in achieving hemostasis. This experience, though, was in a patient population with severe coagulopathy and was based on implantation of an awkward device which was ~2×p0 larger than the pump/reservoir detailed in this protocol (10). In addition, even with these larger devices others have reported excellent safety records in the pre-peritoneal space in the absence of coagulopathy (11, 12) and this continues to be the preferred site of implantation of devices that are too large for the subcutaneous space (13).

Infection. This is a previously mitigated risk. Traditionally one of the biggest barriers to peritoneal implantation of a device has been concerns over infection. While the European clinical data associated with the Medtronic peritoneal insulin pump published by Haveman (9) reported no instances of peritonitis in 381 patient-years of data in 63 patients, we are cognizant of the fact that consequences associated with this condition may be severe. In order to prevent this complication the commercial version of the device will employ two Dacron cuffs to encourage tissue ingrowth to isolate the subcutaneous tunnel from the peritoneal cavity.

The optional curled tip of the catheter may prevent erosion within the body cavity. This tip may be tunneled to the site of implantation. Placement in the peritoneal cavity may involve dissection of the posterior rectus sheath from the peritoneum, angulation of the catheter downward into the true pelvis then perforation of the peritoneum to ensure downward angulation of the catheter into the pelvis. Proximal catheter may then be tunneled subcutaneously to the subcutaneous portion of the implant.

This and the other embodiments may also benefit from an inductive powering or charging circuit. In order to minimize the size of the implant and maximize its life, a small battery may be used that requires recharging on a daily, weekly or monthly basis. Alternatively, the device may be externally powered by placement of an inductive coil over the device during operation, as shown above. Any of the features illustrated in any of the figures or described within this specification may be used alone or in conjunction with other features illustrated in each figure.

While illustrative examples are described above, it will be apparent to one skilled in the art that various changes and modifications may be made therein. Moreover, various apparatuses or procedures described above are also intended to be utilized in combination with one another, as practicable. The appended claims are intended to cover all such changes and modifications that fall within the true spirit and scope of the invention.

While exemplary embodiments have been described in some detail for clarity and understanding and by way of example, a variety of adaptations, modifications, and changes will be obvious to those of skill in the art. Hence, the scope of the present invention is limited solely by the appended claims.

The invention claimed is:

1. A method of determining an analyte concentration within a peritoneal fluid of a human subject, comprising:
    implanting an analyte sensor apparatus in the subject, the apparatus comprising a flexible sensing catheter and a housing, the catheter comprising a lumen with at least one aperture and an analyte sensor in fluid communication with the lumen, the catheter comprising a proximal end attached to the housing, wherein the implanting step comprises positioning the sensing catheter within a true pelvis of the peritoneal space and anchoring the housing at a subcutaneous site proximate the peritoneal space;
    contacting the analyte sensor with a peritoneal fluid sample outside the sensing catheter;
    sensing an analyte concentration in peritoneal fluid sample; and
    transducing the sensed analyte concentration into a transmittable electrical signal.

2. The method of claim 1 wherein implanting an analyte sensor apparatus comprises anchoring the catheter using tissue in-growth cuffs attached to the exterior surface of the catheter to a tissue site within an abdominal wall.

3. The method of claim 1 further comprising flushing the lumen of the catheter with a fluid.

4. The method of claim 3 wherein flushing the lumen of the catheter with a fluid occurs intermittently.

5. The method of claim 3 wherein flushing the lumen of the catheter with a fluid occurs automatically.

6. The method of claim 3 wherein flushing the lumen comprises drawing the fluid from a reservoir.

7. The method of claim 6 wherein the reservoir is refilled intermittently.

* * * * *